United States Patent
Wang et al.

(10) Patent No.: US 8,384,735 B2
(45) Date of Patent: Feb. 26, 2013

(54) IMAGE DISPLAY APPARATUS, IMAGE DISPLAY CONTROL METHOD, AND COMPUTER READABLE MEDIUM HAVING AN IMAGE DISPLAY CONTROL PROGRAM RECORDED THEREIN

(75) Inventors: Caihua Wang, Tokyo (JP); Yoshiyuki Moriya, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 906 days.

(21) Appl. No.: 12/385,737

(22) Filed: Apr. 17, 2009

(65) Prior Publication Data

US 2009/0262998 A1 Oct. 22, 2009

(30) Foreign Application Priority Data

Apr. 17, 2008 (JP) ................................ 2008-107391

(51) Int. Cl.
*G09G 5/14* (2006.01)
(52) U.S. Cl. ...................................................... 345/619
(58) Field of Classification Search .................... 345/619
See application file for complete search history.

(56) References Cited

U.S. PATENT DOCUMENTS

| | | | |
|---|---|---|---|
| 6,577,752 B2 * | 6/2003 | Armato et al. ................. | 382/131 |
| 6,589,164 B1 * | 7/2003 | Flaherty ......................... | 600/121 |
| 7,090,250 B2 * | 8/2006 | Kinoshita et al. .............. | 280/775 |
| 7,865,004 B2 * | 1/2011 | Moriya .......................... | 382/128 |
| 7,949,166 B2 * | 5/2011 | Moriya et al. ................. | 382/128 |
| 7,965,882 B2 * | 6/2011 | Moriya .......................... | 382/131 |
| 8,014,575 B2 * | 9/2011 | Weiss et al. ................... | 382/128 |
| 8,036,439 B2 * | 10/2011 | Moriya .......................... | 382/128 |
| 8,081,811 B2 * | 12/2011 | Moriya .......................... | 382/131 |
| 8,107,699 B2 * | 1/2012 | Hong et al. .................... | 382/128 |
| 8,139,837 B2 * | 3/2012 | Wang ............................. | 382/131 |
| 2005/0010107 A1 * | 1/2005 | Shen .............................. | 600/425 |
| 2005/0265606 A1 * | 12/2005 | Nakamura ..................... | 382/218 |
| 2005/0267366 A1 * | 12/2005 | Murashita et al. ............. | 600/437 |
| 2006/0002632 A1 * | 1/2006 | Fu et al. ......................... | 382/294 |
| 2006/0007244 A1 * | 1/2006 | Matsumoto .................... | 345/619 |
| 2006/0062425 A1 * | 3/2006 | Shen et al. ..................... | 382/100 |

(Continued)

FOREIGN PATENT DOCUMENTS

WO WO-2008/018014 A2 2/2008

OTHER PUBLICATIONS

Steffen Prohaska et al. "Fast visualization of plane-like structures in voxel data" IEEE, 2002.*

(Continued)

*Primary Examiner* — Javid A Amini
(74) *Attorney, Agent, or Firm* — Jean C. Edwards, Esq.; Edwards Neils PLLC

(57) ABSTRACT

Specification is received regarding which structure identifying information, each corresponding to an anatomical structure, is specified as display target structure identifying information to be displayed with a display target image when displaying the display target image, in which the positions of each pixel correspond to positions within an original image. The position of the anatomical structure identified by the structure identifying information is specified, based on structure information, in which structure identifying information that identifies anatomical structures and structure position information that represents the positions of the anatomical structures within the original image are correlated, and the correspondence of positions between the original image and the display target image. The display target structure identifying information is displayed with the display target image such that a user can recognize that the anatomical structure identified by the display target structure identifying information is displayed at the specified position.

10 Claims, 13 Drawing Sheets

U.S. PATENT DOCUMENTS

| | | | |
|---|---|---|---|
| 2006/0171578 A1* | 8/2006 | Novak | 382/131 |
| 2006/0173271 A1* | 8/2006 | Shen et al. | 600/407 |
| 2006/0173272 A1* | 8/2006 | Qing et al. | 600/407 |
| 2007/0110295 A1* | 5/2007 | Shen et al. | 382/131 |
| 2007/0223799 A1* | 9/2007 | Weiss | 382/131 |
| 2008/0159612 A1* | 7/2008 | Fu et al. | 382/131 |
| 2008/0243142 A1* | 10/2008 | Gildenberg | 606/130 |
| 2009/0091567 A1* | 4/2009 | Fu et al. | 345/419 |
| 2009/0174714 A1* | 7/2009 | Nagakura et al. | 345/427 |
| 2010/0086185 A1* | 4/2010 | Weiss | 382/131 |
| 2010/0293505 A1 | 11/2010 | Kiefer et al. | |
| 2011/0123078 A9* | 5/2011 | Weiss et al. | 382/131 |
| 2012/0020538 A1* | 1/2012 | Weiss | 382/131 |
| 2012/0065494 A1* | 3/2012 | Gertner et al. | 600/411 |

OTHER PUBLICATIONS

Hong Shen et al. "Tracing Based segmentation for the labeling of individual rib structures in chest CT colume data" pp. 967-974, 2004.*

K.L. Weiss et al., "Automated Spine Survey Iterative Scan Technique" Radiology, vol. 239, No. 1, pp. 255-262, The Radiological Society of North America, 2006.

* cited by examiner

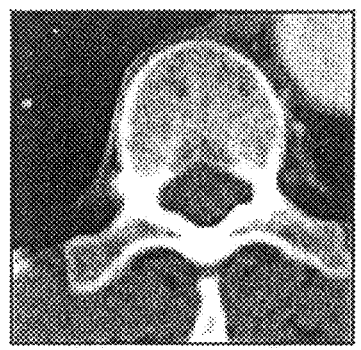
FIG.11
FIG.12
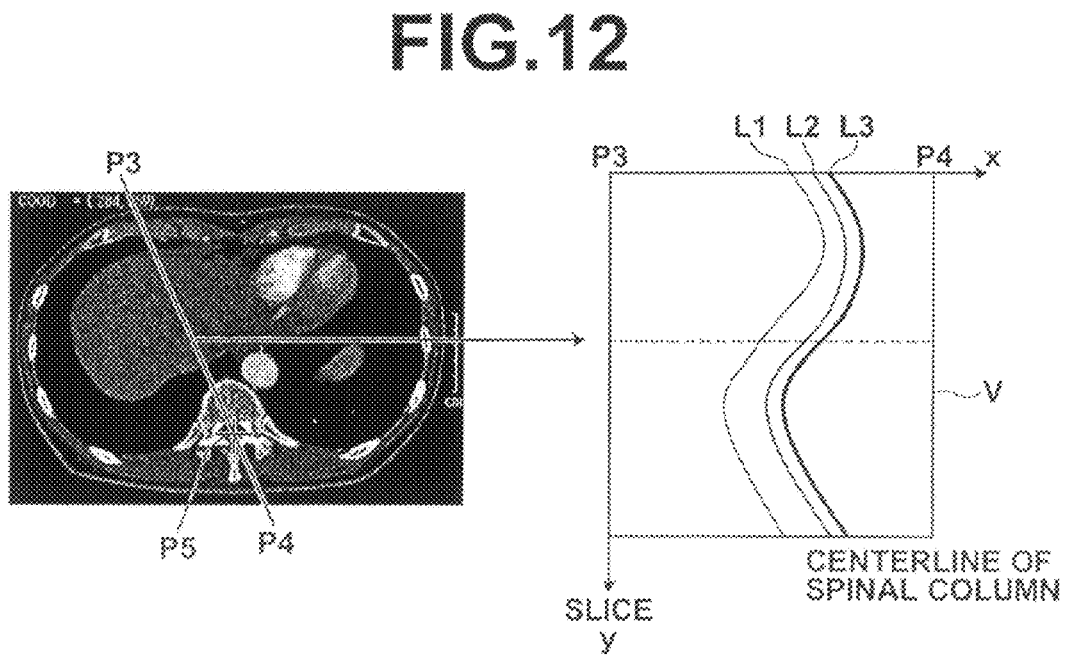

IMAGE DISPLAY APPARATUS, IMAGE DISPLAY CONTROL METHOD, AND COMPUTER READABLE MEDIUM HAVING AN IMAGE DISPLAY CONTROL PROGRAM RECORDED THEREIN

CROSS-REFERENCE TO RELATED APPLICATIONS

The present application claims priority from Japanese Patent Application No. 2008-107391, filed Apr. 17, 2008, the contents of which are herein incorporated by reference in their entirety.

BACKGROUND OF THE INVENTION

1. Field of the Invention

The present invention is related to a technique for displaying images of subjects that include predetermined anatomical structures, along with information that identifies the anatomical structures.

2. Description of the Related Art

There is a known technique for administering image analysis on diagnostic images obtained by MRI imaging that include spinal columns of humans (as disclosed in K. L. Weiss et al., "Automated Spine Survey Iterative Scan Technique", Radiology, Vol. 239, No. 1, pp. 255-262, The Radiological Society of North America, 2006). In this technique, image analysis is administered to extract vertebral disks within the image. Then, symbols for identifying the vertebra (C1 through C7 for the first through seventh cervical vertebrae, T1 through T12 for the first through twelfth thoracic vertebrae, and L1 through L5 for the fifth through fifth lumbar vertebrae) are attached with respect to each of the extracted vertebral disks, and the symbols are displayed to overlap the vertebral disks in the diagnostic images.

During diagnosis based on images of subjects, the positions of diseased portions may be expressed using positional relationships among the diseased portions, surrounding organs, and bones. In this case, physicians are enabled to better understand the positions of diseased portions compared to cases in which the positions of diseased portions are expressed by coordinates of the images, and diagnostic efficiency is improved.

If the information that identifies all of the vertebral disks are displayed to overlap the diagnostic images as in the technique disclosed by K. L. Weiss et al., the positional relationships among diseased portions and the vertebral disks becomes easy to understand. However, a great number of pieces of identifying information are displayed within diagnostic images, which deteriorates the visibility of the portions of the images at which the vertebral disks are pictured, and acts as a barrier to diagnosis.

SUMMARY OF THE INVENTION

The present invention has been developed in view of the foregoing circumstances. It is an object of the present invention to provide an image display apparatus, an image display control method, and a computer readable medium in which an image display control program is stored, that reduces the deterioration in visibility of diagnostic images during image diagnosis in cases that information that identifies predetermined anatomical structures within diagnostic images are displayed along with the diagnostic images.

An image display apparatus of the present invention is characterized by comprising:

image display means for displaying a two dimensional display target image, in which the positions of each pixel are enabled to correspond to positions within an original image that represents a subject in two or more dimensions, based on the original image;

structure information obtaining means for obtaining structure information, in which structure identifying information that identifies each of a plurality of predetermined anatomical structures within the subject and structure position information that represents the positions of the anatomical structures within the original image are correlated;

structure identifying information specifying means for receiving specification regarding which of the structure identifying information, each corresponding to an anatomical structure, is specified as display target structure identifying information to be displayed along with the display target image; and structure position specifying means for specifying the position of the anatomical structure, which is identified by the structure identifying information, within the display target image, based on the structure information and the correspondence of positions between the original image and the display target image;

the image display means displaying the display target structure identifying information along with the display target image such that a user can visually recognize that the anatomical structure which is identified by the display target structure identifying information is displayed within the display target image at the position specified by the structure position specifying means.

An image display control method of the present invention is a method for displaying a two dimensional display target image, in which the positions of each pixel are enabled to correspond to positions within an original image that represents a subject in two or more dimensions, based on the original image, characterized by comprising the steps of:

obtaining structure information, in which structure identifying information that identifies each of a plurality of predetermined anatomical structures within the subject and structure position information that represents the positions of the anatomical structures within the original image are correlated;

receiving specification regarding which of the structure identifying information, each corresponding to an anatomical structure, is specified as display target structure identifying information to be displayed along with the display target image;

specifying the position of the anatomical structure, which is identified by the structure identifying information, within the display target image, based on the structure information and the correspondence of positions between the original image and the display target image; and displaying the display target structure identifying information along with the display target image such that a user can visually recognize that the anatomical structure which is identified by the display target structure identifying information is displayed within the display target image at the position specified by the structure position specifying step.

A computer readable medium of the present invention is that on which a program that causes a computer to execute the image display control method of the present invention is recorded.

Note that those who are skilled in the art would know that computer readable media are not limited to any specific type of device, and include, but are not limited to: floppy disks, CD's, RAM's, ROM's, hard disks, magnetic tapes, and internet downloads, in which computer instructions can be stored and/or transmitted. Transmission of the computer instructions through a network or through wireless transmission means is also within the scope of the present invention. Additionally, computer instructions include, but are not limited to: source, object, and executable code, and can be in any language, including higher level languages, assembly language, and machine language.

Hereinafter, the details of the present invention will be described.

The "display target image" may be any type of image, as long as the positions of each pixel therein are enabled to correspond to positions within the original image. As a specific example, the original image may be a three dimensional image constituted by an agglomeration of sectional images taken at a plurality of points along a structural axis that extends in a predetermined direction. In this case, the display target image may be a sectional image taken at one of the plurality of points. As another example, the original image may be a two dimensional image. In this case, the display target image may be the same image as the original image, or a portion which is cut out from the original image.

It is preferable for bones to be employed as the "plurality of predetermined anatomical structures within the subject".

Specific examples of the "structure identifying information" include the names of the anatomical structures, numbers that represent the anatomical structures, and symbols that represent the anatomical structures.

The correlation between the "structure identifying information . . . , and structure position information" is a "one to one" correspondence in the case that the original image is expressed in three dimensions or less. This is because a single anatomical structure is present at a single specific position in this case. However, in the case that the original image is a four dimensional image that represents a three dimensional video of a subject, there is a possibility that a single anatomical structure will be present at different positions along the temporal phase. Therefore, the correlation between the structure identifying information and structure position information may become a "one to many" correspondence. In this case, a single piece of structure identifying information may be correlated with the position of a single anatomical structure at each temporal phase of the original image. Then, information regarding the position of the anatomical structure at a temporal phase corresponding to the temporal phase of a display target image may be employed to specify the position of the anatomical structure within the display target image.

The process for "specifying the position of the anatomical structure, which is identified by the structure identifying information, within the display target image, based on the structure information and the correspondence of positions between the original image and the display target image" assumes the following. Each pixel of the display target image is correlated to a specific position within the original image. Meanwhile, the position of each of the anatomical structures within the original image, which are identified by the structure identifying information, is specified by the structure position information. Therefore, it is assumed that the positions of the anatomical structures which are identified by the structure identifying information within the display target image are specifiable indirectly via the positional coordinate system of the original image. Accordingly, it is possible to specify the positions of the anatomical structures which are identified by the structure identifying information within the display target image by the indirect correlation.

The "structure information" may be obtained by image analyzing processes that recognize the anatomical structures within the original image. Alternatively, the "structure information" may be obtained by a user who views a two dimensional image obtained from the original image and manually sets the positions of the anatomical structures within the image. In addition, the "structure information" may be label images that represent the structure identifying information and the structure position information within the original image. Here, a "label image" is a multiple valued image, in which a label value (structure identifying information), which is different for each anatomical structure, is added to the position and region (structure position information) of each of the anatomical structures within the original image.

The specification of the "display target structure identifying information" may be specification of a structure group identifying information that specifies a group constituted by a plurality of anatomical structures. In this case, the pieces of structure identifying information that identify the plurality of anatomical structures included in the group are specified as the display target structure identifying information. Specific examples of structure group identifying information include: a "ribs" group that includes the first through twelfth left and right ribs; a "vertebral bones" group that includes the first through seventh cervical vertebrae, the first through twelfth thoracic vertebrae, and the first through fifth lumbar vertebrae; a "left ribs" group, and a "cervical vertebra" group.

In the case that a structure group identifying information is specified, a representative structure identifying information to be displayed along with the display target image from among the plurality of pieces of structure identifying information, each of which identifies an anatomical structure included in a group, may be determined based on a predetermined rule. In this case, the image display means may display only the determined representative structure identifying information from among the structure identifying information of the plurality of anatomical structures that belong to the group along with the display target image. The predetermined rule may be defined by at least one of: the distribution of positions, which have been specified by the structure position specifying means, of the plurality of anatomical structures included in the group which is identified by the specified structure group identifying information within the target display image; the structure identifying information of the plurality of anatomical structures; and the type of the display target image. That is, it is preferable for the predetermined rule to be defined such that an optimal piece of structure identifying information is selected as the representative structure identifying information to be displayed along with the display target image, according to: which direction the sectional image, which is the display target image, is a view from (the type of the display target image); the anatomical structure which is the display target of the structure identifying information; and where in the display target image the anatomical structures identified by the structure identifying information are displayed (the distribution of positions of the anatomical structures).

Specification may be received regarding whether only the representative structure identifying information is to be displayed along with the display target image, or the structure identifying information for all of the anatomical structures that belong to the group which is identified by the structure group identifying information is to be displayed.

Specification may also be received regarding the display position of the display target structure identifying information.

The specification regarding the display position may be received such that the display target structure identifying information is displayed in the vicinity of the anatomic structure which is identified by the display target structure identifying information. Here, the specific range of positions which is defined by the term "vicinity" may be a uniform range which is set in advance. Alternatively, the range may be determined according to the type of the anatomical structure which is identified by the display target structure identifying information or the like.

It is preferable for the specification of the display target structure identifying information, whether only the representative structure identifying information is to be displayed, and the display position of the structure identifying information to be realized via a user interface for receiving specifications by selection from among a plurality of selectable options.

The present invention displays a two dimensional display target image, in which the positions of each pixel are enabled to correspond to positions within an original image that represents a subject in two or more dimensions, based on the original image. Specification is received regarding which of the structure identifying information, each corresponding to an anatomical structure, is specified as display target structure identifying information to be displayed along with the display target image. The position of the anatomical structure, which is identified by the structure identifying information, within the display target image is specified, based on the structure information, in which structure identifying information that identifies each of a plurality of predetermined anatomical structures within the subject and structure position information that represents the positions of the anatomical structures within the original image are correlated, and the correspondence of positions between the original image and the display target image. The display target structure identifying information is displayed along with the display target image such that a user can visually recognize that the anatomical structure which is identified by the display target structure identifying information is displayed within the display target image at the specified position. Accordingly, only pieces of structure identifying information which are desired by the user are displayed along with the display target image, from among the plurality of pieces of structure identifying information corresponding to the plurality of anatomical structures. Therefore, deterioration in visibility of the display target image due to the structure identifying information being overlapped thereon and displayed can be reduced, while maintaining the ease with which the positions of the anatomical structures identified by the specified structure identifying information are understood.

BRIEF DESCRIPTION OF THE DRAWINGS

FIG. 11 is a diagram that illustrates an example of a tomographic image of a vertebra.

FIG. 12 is a diagram for explaining a method for calculating the centerline of a spinal cord.

BEST MODE FOR CARRYING OUT THE INVENTION

Hereinafter, a process in which identifying information that identifies vertebral bones and ribs are displayed along with a display target axial tomographic image that constitutes a portion of a three dimensional original image obtained by CT or MRI will be described as an embodiment of the present invention, with reference to the attached drawings. Note that in the following description, the identifying information will be referred to as vertebral bone numbers and rib numbers. In cases that it is not particularly necessary to clearly distinguish between the two, they will simply be referred to as bone numbers. In the following description, the vertebral bone numbers will be referred to as first through seventh cervical vertebrae, first through twelfth thoracic vertebrae, first though fifth lumbar vertebrae. The ribs numbers will be referred to as first through twelfth left ribs, and first through twelfth right ribs. Alternatively, symbols such as C1 through C7, T1 through T12, and L1 through L5 may be employed for the vertebral bones.

Figure 1:
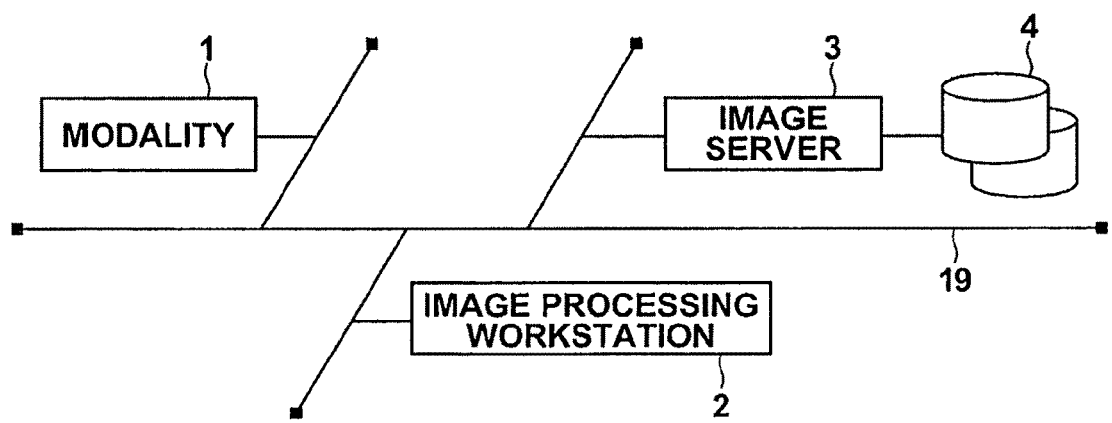
FIG. 1 is a diagram that schematically illustrates the construction of a medical information system, in which an image processing work station that realizes an embodiment of the present invention is incorporated.

FIG. 1 is a diagram that schematically illustrates the construction of a medical information system, in which an image processing work station 2 is incorporated. As illustrated in FIG. 1, the system is constituted by: an imaging apparatus 1 (imaging modality 1) for medical images; the image processing work station 2; an image server 3; and an image database 4. The components of the system are connected via a network 19 such that they can communicate with each other. The image processing work station 2 and the image server 3 are controlled by programs which are installed from a recording medium such as a CD-ROM. Alternatively, the programs may be downloaded from the memory device of a server which is connected to the image processing work station 2 and the image server 3 via a network such as the Internet, and then installed in the image processing work station 2 and the image server 3.

The imaging modality 1 includes an apparatus that generates image data that represents a subject by imaging the subject, and outputs the image data with information, such as examination information and patient information, attached thereto. The attached information is of a standardized format such as the DICOM format, or a format unique to the manufacturer of the imaging modality 1. Specific examples of the imaging modality 1 include: CT (Computed Tomography); MRI (Magnetic Resonance Imaging); PET (Positron Emission Tomography); and ultrasound imaging apparatuses. Note that in the present invention, the image data are three dimensional images obtained by CT, MRI and the like that represent subjects, and are constituted by an agglomeration of axial tomographic images having predetermined slice intervals and slice widths.

The image processing work station 2 is a computer equipped with a processing apparatus, at least one high definition display, input devices such as a keyboard and a mouse, and a communications interface that communicates with the image server 3 and the like via the network 19. A software program that causes the vertebral bone numbers and/or the rib numbers to be displayed with a display target image is installed in the image processing work station.

A software program that provides the functions of a general purpose DBMS (Data Base Management System) having comparatively high processing performance is installed in the image server 3. The image server 3 is also equipped with a high capacity storage that constitutes the image database 4. The storage may be: a high capacity hard disk device which is connected to the image server 3 via a data bus; an NAS (Network Attached Storage) which is connected to the network 19; or a disk device which is connected to an SAN (Storage Area Network). The image server 3 is also equipped with a communications interface for communicating with the imaging modality 1, the image processing work station 2 and the like via the network 19. The image server 3 receives image data that represent images imaged and obtained by the modality 1 and registers the image data to the image database 4. The image server 3 also extracts image data that matches search criteria input through the image processing workstation from among image data registered in the image database 4, and transmits the extracted image data to the image processing workstation 2.

The network 19 is a local area network that connects various apparatuses within a hospital. However, in the case that an image reading work station is provided at a different hospital or clinic, the network 19 may be a network that connects local area networks of different hospitals via the Internet or via dedicated networks. In either case, it is desirable for the network 19 to be that which enables high speed transfer of image data, such as an optical fiber network.

Figure 2:
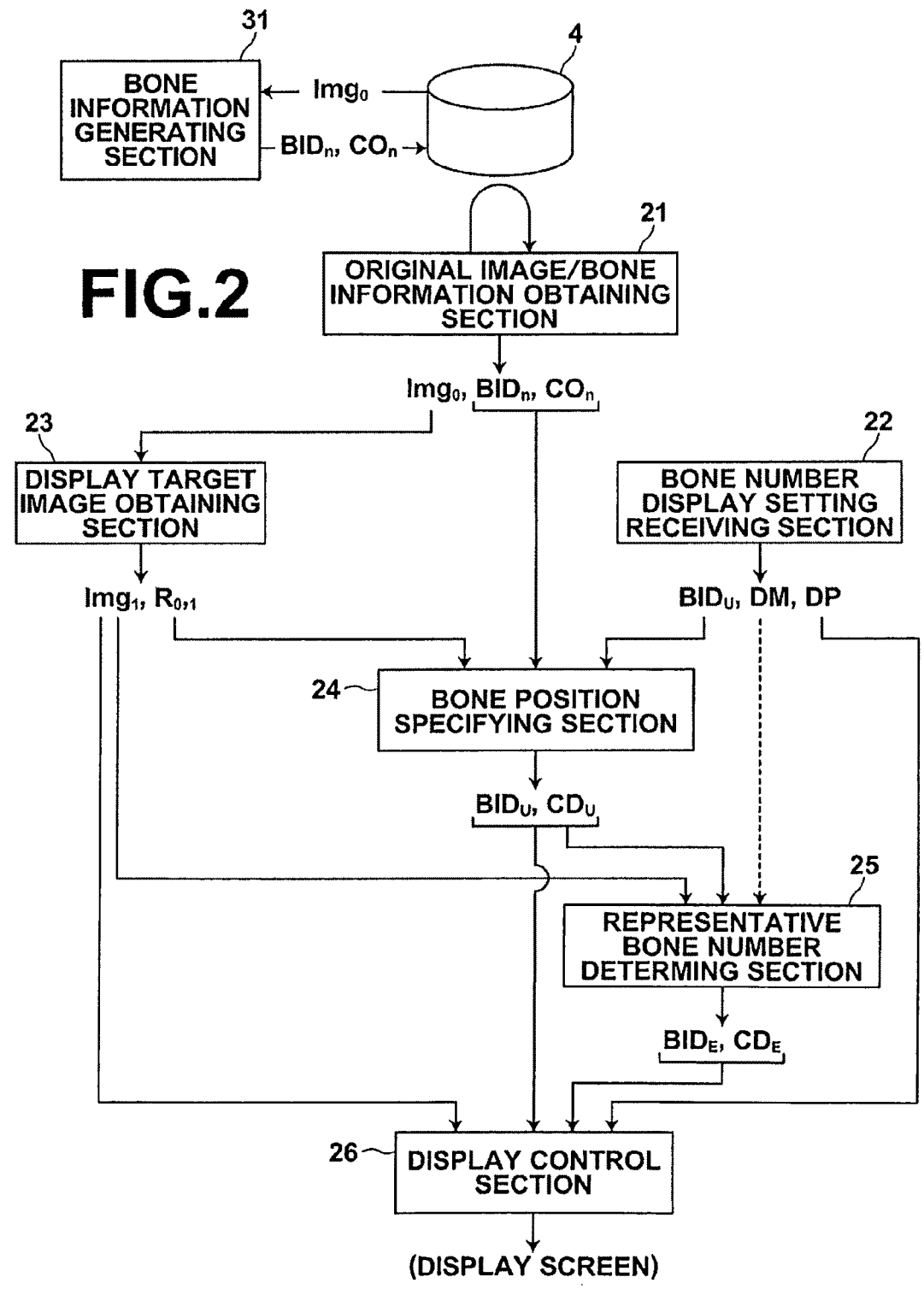
FIG. 2 is a functional block diagram of the image processing work station that realizes the image display process, which is the embodiment of the present invention.

FIG. 2 is a diagram that illustrates the functions of the image display process, which is the embodiment of the present invention, from among the functions that the image processing work station 2 performs. As illustrated in FIG. 2, the image display process, which is the embodiment of the present invention, is realized by: an original image/bone information obtaining section 21; a bone number display setting receiving section 22; a display target image obtaining section 23; a bone position specifying section 24; a representative bone number determining section 25; and a display control section 26. Control of the determination of data to be processed by each processing section, control of the processing order of each processing section, and the like are performed by a control section 27 (not shown), which is realized by the main program of the image display control program of the present invention being executed. Note that in the present embodiment, information (examination ID and series ID) that specifies image data of a three dimensional image which is the target of processing is input as start parameters when the program is started up.

The original image/bone information obtaining section 21 transmits a search request to the image server 3, using the examination ID and the series ID as search criteria. The image server 3 searches the image database in response to the search request and extracts image data $Img_0$ (hereinafter, images and image data that represent images will be referred to with the same reference labels) that represents the three dimensional image which is the target of processing and is correlated to the examination ID and the series ID. Then, the image data $Img_0$ is transmitted to the image processing work station 2. The original image/bone information obtaining section 21 receives the image data $Img_0$, and stores it in a predetermined region of a hard disk of the image processing work station 2. The image data may be stored as a collection of image files, each representing an axial tomographic image that constitutes the three dimensional image. The three dimensional image data $Img_0$ also includes attached information, such as: bone information BI that includes bone numbers $BID_n$ (n is a suffix that identifies each bone) for vertebral bones and ribs within the image, and position information $CO_n$ regarding the bones identified by the bone numbers (hereinafter, referred to as "original bone position information"); and slice numbers. Each of the processing sections are capable of obtaining information necessary to perform the processes assigned thereto.

Here, the bone information BI is generated by a bone information generating section 31 in advance, and added to the three dimensional image data $Img_0$ as attached information. That is, the bone information generating section 31 performs an image analyzing process on the three dimensional image data $Img_0$, which is obtained by the image server 3 from the image database 4. The bone information generating section 31 detects vertebral bones and ribs within the image, recognizes the vertebral bone numbers and the rib numbers for each of the detected vertebral bones and ribs, attaches bone numbers $BID_n$ and original bone position information $CO_n$ regarding the bones identified by the bone numbers $BID_n$ to the three dimensional image data $Img_0$ as attached information, and stores the three dimensional image data $Img_0$ and the attached information in the image database 4. Because the bones are three dimensional anatomical structures, the original bone position information $CO_n$ is information that represents three dimensional regions. Note that an example of the image analyzing process will be described later as a supplemental description.

Figure 4:
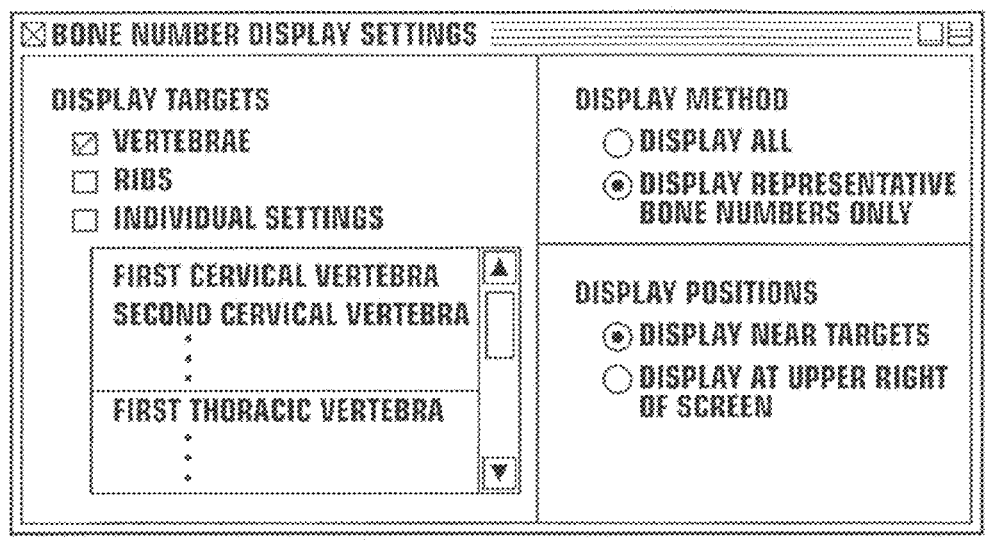
FIG. 4 is a diagram that illustrates a bone number display setting screen as an example of a graphical user interface.

The bone number display setting receiving section 22 provides a graphical user interface for receiving specification of bone numbers $BID_u$ (hereinafter, referred to as display target bone numbers $BID_u$) to be displayed along with a display target image $Img_1$ (to be described layer in the explanation of the display target image obtaining section 23), a display method DM for the display target bone numbers $BID_u$, and display positions DP of the display target bone numbers $BID_u$. FIG. 4 is a diagram that illustrates a bone number display setting screen, as an example of the graphical user interface.

Check boxes and a list box for receiving selection of display target bone numbers for the display target bone numbers $BID_u$ are displayed at the left side of the screen of FIG. 4. Selection of display target bone numbers $BID_u$ is received by a user operating a mouse or the like to check a check box corresponding to bone numbers to be displayed. Note that three check boxes are provided, to enable selection of only "Vertebral Bones", only "Ribs", "Vertebral Bones" and "Ribs", and only "Individual Settings". Specifically, in the case that "Vertebral Bones" is selected, the bone numbers of all of the individual vertebral bones, that is, the first through seventh cervical vertebrae, the first through twelfth thoracic vertebrae, and the first through fifth lumbar vertebrae, are selected as display targets. In the case that "Ribs" is selected, the bone numbers of the left and right first through twelfth ribs are selected as display targets. In the case that "Individual Settings" is selected, selection of display target bone numbers $BID_u$ is received by the user operating a mouse or the like to click on bone numbers that the user desires to be displayed, from among the bone numbers in the list box at the lower left of the screen. The selected bone numbers are highlighted and displayed. Note that it is possible for the user to select a plurality of bone numbers from within the list box.

Radio buttons for receiving selection of the display method DM for the display target bone numbers $BID_u$ selected in the manner described above are displayed at the upper right of the screen of FIG. 4. Selection of the display method DM is received by the user operating a mouse or the like to select either "Display All" or "Display Representative Bone Number Only". Here, in the case that "Display All" is selected, if the bones corresponding to the display target bone numbers $BID_u$ are present in the display target image $Img_1$, the bone numbers are displayed along with the display target image $Img_1$. On the other hand, in the case that "Display Representative Bone Number Only" is selected, a representative bone number $BID_E$ is determined from among the display target bone numbers $BID_U$ which have been selected as described above and which are present within the display target image $Img_1$, based on a predetermined rule. The method by which the representative bone number $BID_E$ is determined will be described later in the description of the process performed by the representative bone number determining section 25. Note that the display method DM may be set to be selectable only when "Vertebral Bones" and/or "ribs" are selected as the display target bone numbers $BID_U$.

Radio buttons for receiving selection of the display position DP of the display target bone numbers $BID_U$ selected as described above are displayed at the lower right of the screen of FIG. 4. Selection of the display position DP is received by the user operating a mouse or the like to click either of the radio buttons for "Display Near Target" and "Display at Upper Right of Image". Here, in the case that "Display Near Target" is selected, bone numbers are displayed in the vicinities of bones which are identified thereby in the display target image $Img_1$ (refer to FIG. 6). The method by which the specific display positions are determined will be described later in the description of the process performed by the display control section 26. On the other hand, in the case that "Display at Upper Right of Image" is selected, bone numbers are displayed at a fixed position at the upper right of the display target image $Img_1$.

The display target image obtaining section 23 obtains image data that represents an axial tomographic image corresponding to the slice number ($m_0$), which has been input as a startup parameter, from the three dimensional original image data $Img_0$ as the display target image $Img_1$. At this time, correspondence information $R_{0,1}$ that represents what position within the three dimensional original image an arbitrary position within the axial tomographic image having the slice number $m_0$ corresponds to is also obtained. In the present embodiment, a position ($x_1$, $y_1$) within the display target axial tomographic image corresponds to a position ($x_1$, $y_1$, $m_0$) within the three dimensional original image.

The bone position specifying section 24 specifies the positions of bones identified by the display target bone numbers $BID_U$ within the display target image $Img_1$, using the bone numbers $BID_n$ and the original bone position information $CO_n$ within the three dimensional original image $Img_0$, the correspondence information $R_{0,1}$ between the three dimensional original image $Img_0$ and the display target image $Img_1$, and the display target bone numbers $BID_U$ as inputs. The bone position specifying section 24 then outputs position information $CD_U$ (hereinafter, referred to as display bone position information $CD_U$) that represents the specified positions.

Specifically, first, the bone position specifying section 24 obtains display bone position information $CD_n$, that represents the positions of each bone identified by the bone number information $BID_n$ in the display target image $Img_1$ that represents the axial tomographic image at slice number $m_0$, based on the original bone position information $CO_n$ of the three dimensional original image $Img_0$ and the correspondence information $R_{0,1}$. That is, in the present embodiment, the display bone position information $CD_n$ is extracted from the original bone position information $CO_n$ of the three dimensional original image $Img_0$, at the slice number $m_0$. Accordingly, display position information $CD_n$ does not exist for bones which are not present in the display target image $Img_1$ in other words, bones for which the region represented by original position information $CO_n$ does not include positions at slice number $m_0$.

Next, the bone position specifying section 24 specifies the display bone position information $CD_U$ of the bones identified by the display target bone numbers $BID_U$ within the display target image $Img_1$, based on the display target bone numbers $BID_U$ and the display bone position information $CD_n$ for each of the bones. Here, the display position information $CD_n$ does not exist for bones which are identified by the display target bone numbers $BID_U$ but are not present in the display target image $Img_1$.

Note that the bone position specifying section 24 may specify the display bone position information $CD_U$ of bones to be displayed, by obtaining the original bone position information $CO_U$ of bones which are identified by the display target bone numbers $BID_U$, and then performing conversion of the original bone position information $CO_U$, using the correspondence information $R_{0,1}$.

Figure 5:
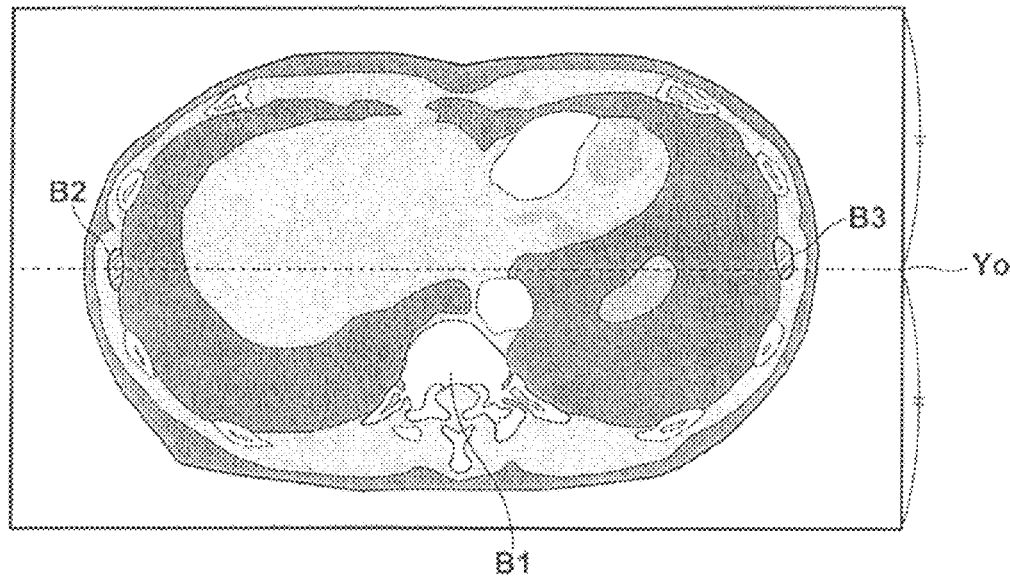
FIG. 5 is a diagram that schematically illustrates an example of a method for determining a representative bone number within an axial tomographic image.

The representative bone number determining section 25 determines a representative bone number $BID_E$ to be displayed along with the display target image $Img_1$, in the case that "Display Representative Bone Number Only" is selected as the display method DM. The representative bone number determining section 25 determines the representative bone number $BID_E$ based on a predetermined rule, using the display target image data $Img_1$, the display target bone numbers $BID_U$, and the display bone position information $CD_U$ for bones which are identified by the display target bone numbers $BID_U$ as inputs. The representative bone number determining section 25 outputs the representative bone number $BID_E$ and display bone position information $CD_E$ for the bone identified by the representative bone number $BID_E$. Here, specific examples of the predetermined rule include: "in the case that the display target image $Img_1$ is an axial tomographic image, and the display target bone numbers $BID_U$ include all vertebral bones, the bone number for vertebra B1 which is displayed in the display target image $Img_1$ is the representative bone number $BID_E$"; and "in the case that the display target image $Img_1$ is an axial tomographic image, and the display target bone numbers $BID_U$ include all ribs, the bone numbers for ribs B2 and B3 which are closest to the center point in the vertical direction of the display target image $Img_1$ (the front to back direction of the subject) are designated as the representative bone numbers $BID_E$", as illustrated in FIG. 5. In the case of the latter rule regarding the ribs, the representative bone number determining section 25 determines the display target bone number $BID_U$ of a bone with display bone position information $CD_U$ having the least difference in position from a central position $Y_0$ in the vertical direction of the display target image $Img_1$ as the representative bone number $BID_E$.

Figure 6:
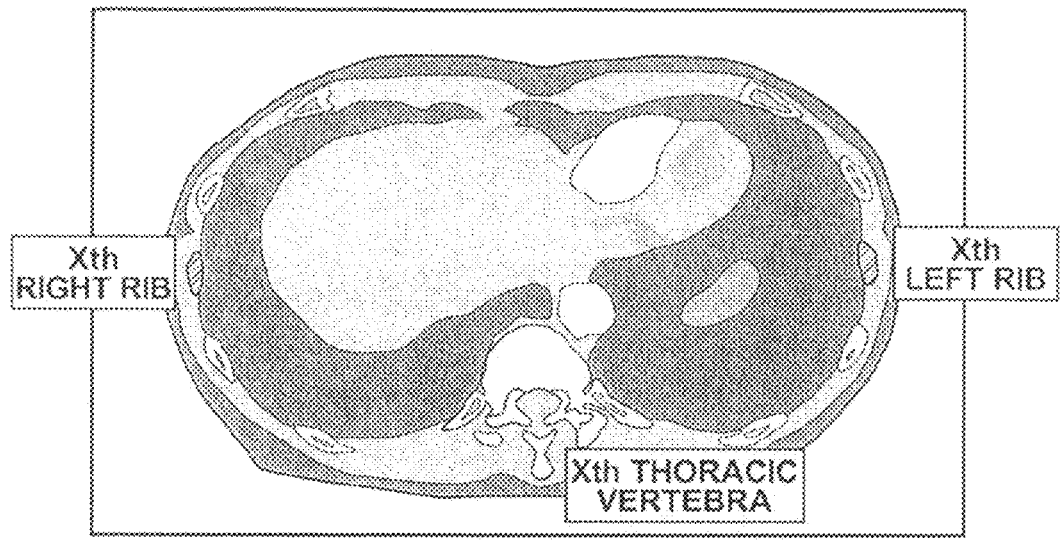
FIG. 6 is a diagram that illustrates an example of the manner in which bone numbers are displayed within an axial tomographic image.

The display control section 26 causes the display target image $Img_1$ to be displayed on a display screen, along with the display target bone numbers $BID_U$ or the representative bone numbers $BID_E$ at positions specified by the display position information DP. The display control section 26 uses the display target image data $Img_1$, the display target bone numbers $BID_U$ and the display bone position information $CD_U$ for the bones identified by the display target bone numbers $BID_U$, or the display target image data $Img_1$, the representative bone numbers $BID_E$ and the display bone position information $CD_E$ for the bones identified by the representative bone numbers $BID_E$ as inputs. Here, even if bones are specified as display target bone numbers $BID_U$, if the bones are not present in the display target image $Img_1$, display position information $CD_n$ does not exist for these bones. Therefore, the bone numbers corresponding to these bones are not displayed along with the display target image $Img_1$. FIG. 6 is a diagram that illustrates an example of display in the case that "Display Near Target" is selected as the display positions DP. As illustrated in FIG. 6, the display control section 26 determines the display positions of each bone number, based on the display target bone numbers $BID_U$ or the representative bone numbers $BID_E$ and the display bone position information $CD_U$ or $CD_E$ corresponding thereto, according to a preset rule. An example of the preset rule is: "in the case that the display target image $Img_0$ is an axial tomographic image, rib numbers are displayed to the exterior of the ribs represented by the rib numbers, and a vertebra number is displayed toward the lower right (or the lower left) of the vertebra represented by the vertebra number". Then, the display control section 26 overlaps the display target bone numbers $BID_U$ or the representative bone numbers $BID_E$ onto the display target image $Img_1$ and displays the display target image $Img_1$. On the other hand, in the case that "Display at Upper Right of Image" is selected as the display position DP, overlapped display such as that illustrated in FIG. 6 is not performed, and the display target bone numbers $BID_U$ or the representative bone numbers $BID_E$ are displayed at a fixed position outside the display target image $Img_1$ toward the upper right thereof. In this case, a configuration may be adopted wherein a plurality of bone numbers are not displayed simultaneously. It is preferable for the bone number to be displayed in response to specifying operations within the display target image $Img_1$ by the user. An example of such a configuration is that in which the bone number of a bone corresponding to the display target bone numbers $BID_U$ or the representative bone numbers $BID_E$ is displayed at the upper right of the display target image $Img_1$ when the bone is clicked on.

Figure 3:
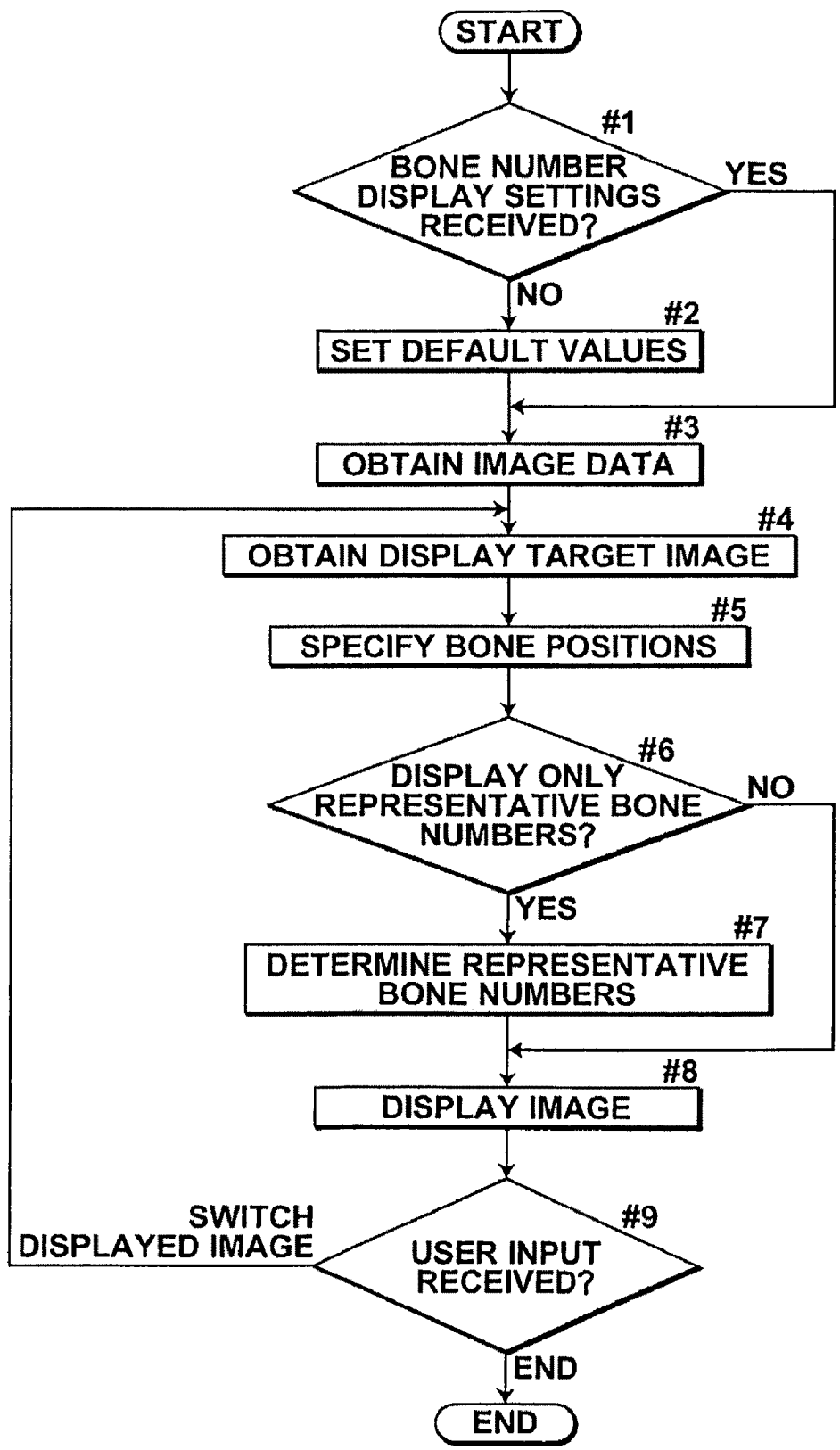
FIG. 3 is a flow chart that illustrates the steps of an image display process, which is the embodiment of the present invention.

Next, the steps of the image display process, which is the embodiment of the present invention, will be described with reference to the flow chart of FIG. 3. The steps of the process are realized by control exerted by the control section 27 of the image processing work station 2.

First, when the image display program of the present invention is started up at the image processing work station 2, the control section 27 calls on the bone number display setting receiving section 22. The bone number display setting screen is caused to be displayed on the display screen, and the bone number display setting receiving section 22 receives specification of display target bone numbers $BID_U$, the display method DM, and the display position DP (step 1). The display target bone numbers $BID_U$, the display method DM, and the display position DP specified by the user are stored in a predetermined memory region of the image processing workstation (step 1: YES). On the other hand, in the case that the user did not input any specifications, (step 1: NO), the bone number display setting receiving section 22 stores predefined default display target bone numbers $BID_U$, a predefined default display method DM, and a predefined default display position DP are stored in the predetermined memory region (step 2). Thereafter, the bone number display setting receiving section 22 transmits a "reception completed" message to the control section 27.

When the "reception completed" message is received, the control section 27 calls on the original image/bone information obtaining section 21, and transmits the examination ID, the series ID and the like which are obtained from the startup parameters thereto. The original image/bone information obtaining section 21 transmits a search request to the image server 3 with the examination ID, the series ID, and the like as search keys. The image server 3 extracts three dimensional original image data $Img_0$ and bone information BI (bone numbers $BID_n$ and original bone position information $CO_n$) by searching the image database 4, and transmits the three dimensional original image data $Img_0$ and the bone information BI to the original image/bone information obtaining section 21. The original image/bone information obtaining section 21 receives the three dimensional image data $Img_0$ and the bone information BI from the image server 3, stores them in a predetermined region of the hard disk of the image processing work station 2, and transmits a "three dimensional data $Img_0$ obtainment completed" message to the control section 27 (step 3).

When the "three dimensional data $Img_0$ obtainment completed" message is received, the control section 27 calls on the display target image obtaining section 23, and transmits the slice number $m_0$ of the display target axial tomographic image, which is included in the startup parameters, and the storage location of the three dimensional original image data $Img_0$ thereto. The display target image obtaining section 23 obtains image data that represents an axial tomographic image corresponding to the slice number $m_0$ from the three dimensional original image data $Img_0$ as a display target image $Img_1$. The display target image obtaining section 23 stores the display target image $Img_1$ and correspondence information $R_{0,1}$ in a predetermined memory region, and transmits a "display target image obtainment completed" message to the control section 27 (step 4). Note that in the present embodiment, the slice number $m_0$ is stored in the predetermined memory region as the correspondence information $R_{0,1}$.

When the "display target image obtainment completed" message is received, the control section 27 calls on the bone position specifying section 24, and transmits bone number information $BID_n$, original bone position information $CO_n$ for each bone, the correspondence information $R_{0,1}$, and the display target bone numbers $BID_U$ thereto. The bone position specifying section 24 specifies the positions of bones identified by the display target bone numbers $BID_U$ within the display target image $Img_1$, based on the transmitted information. The bone position specifying section 24 then stores display bone position information $CD_U$ in a predetermined memory region, and transmits a "bone position specifying process completed" message to the control section 27 (step 5).

When the "bone position specifying process completed" message is received, the control section 27 judges whether "Display Representative Bone Number Only" has been selected as the display method DM at step 1 (step 6). In the case that the judgment at step 6 is affirmative (step 6: YES), the control section 27 calls on the representative bone number determining section 25, and transmits the display target image data $Img_1$, the display target bone numbers $BID_U$, and the display bone position information $CD_U$ thereto. The representative bone number determining section 25 determines the representative bone number $BID_E$ to be displayed along with the display target image $Img_0$ from among the display target bone numbers $BID_u$, based on the information transmitted thereto. The representative bone number determining section 25 stores the representative bone number $BID_E$ and display bone position information $CD_E$ for the bone identified by the representative bone number $BID_E$ in a predetermined memory region, and transmits a "representative bone number determination completed" message to the control section 27 (step 7). When the "representative bone number determination completed" message is received, the control section 27 proceeds to the next step. On the other hand, if "Display All" is selected as the display method DM (step 6: NO), step 7 is skipped.

Next, the control section 27 calls on the display control section 26, and transmits the representative bone number $BID_E$ and the display bone position information $CD_E$ of the bone identified by the representative bone number $BID_E$ along with the display target image data $Img_1$ and the display position information DP thereto in the case that they are stored in the memory. Otherwise, the control section 27 transmits the display target bone numbers $BID_U$ and the display bone position information $CD_U$ of the bones identified by the display target bone numbers $BID_U$ along with the display target image data $Img_1$ and the display position information DP to the display control section 26. The display control section 26 causes the display target image $Img_1$ to be displayed on the display screen, and also displays the transmitted bone number ($BID_E$ or $BID_U$) according to the display position information DP (step 8). In the case that "Display All" is selected as the display method DM for the display target bone numbers $BID_U$, the display target bone numbers $BID_U$ of bones are displayed along with the display target image $Img_1$, if they are present within the display target image $Img_1$. On the other hand, in the case that "Display Representative Bone Number Only" is selected as the display method DM for the display target bone numbers $BID_U$, only the representative bone numbers $BID_E$, which are determined from among the bones identified by the selected display target bone numbers $BID_U$ and are present within the display target image $Img_1$, are displayed along with the display target image $Img_1$.

Here, the user may perform an operation to switch the image which is being displayed on the display screen. For example, the user may select a display target image $Img_1$ by a clicking operation using a mouse, then switch the display to an axial tomographic image having a slice number $m_0+1$, by operating the scrolling wheel of the mouse. Alternatively, the user may cause an operation menu to be displayed by operating a mouse or the like, then select a desired type of image (an axial image having a slice number $m_0+1$, for example) from the displayed menu, to switch the display from the display target image $Img_1$ to a different image. If the control section 27 detects such a switching operation (step 9: Switch Displayed Image), information that specifies the next image to be displayed (slice number $m_0+1$ in the example described above) is obtained. The obtained information is transmitted to the display target image obtaining section 23, and the display target image obtaining section 23 is caused to obtain correspondence information $R_{0,2}$ (slice number $m_0+1$ in the example described above) from the three dimensional original image (step 4). Bone number information $BID_n$, original bone position information $CO_n$ for each bone, the correspondence information $R_{0,2}$, and the display target bone numbers $BID_U$ are transmitted to the bone position specifying means 24. The bone position specifying means 24 is caused to specify display bone position information $CD_U$ (step 5). In the case that the "Display Representative Bone Number Only" is selected as the display method DM (step 6: YES), the representative bone number determining section 25 receives the display target image data $Img_2$, the display target bone numbers $BID_U$, and the display bone position information $CD_U$. The representative bone number determining section 25 is caused to determine the representative bone number $BID_E$ to be displayed along with the display target image $Img_2$ from among the display target bone numbers $BID_u$ (step 7). Then, the display target image $Img_2$, the bone numbers ($BID_E$ or $BID_U$), the display bone position information ($CD_U$ or $CD_E$), and the display position information DP are transmitted to the display control section 26, and the display target image $Img_2$ is caused to be displayed on the display screen, along with the bone numbers ($BID_E$ or $BID_U$), according to the display position information DP (step 8). Bone numbers corresponding to the next display target image $Img_2$ are displayed in this manner. In the case that the user performs another operation to switch the image which is to be displayed on the display screen, the control section 27 detects the operation (step 9: Switch Displayed Image) the processes of step 4 through step 8 are repeated, and a next image is displayed along with the bone numbers ($BID_E$ or $BID_U$), according to display position information DP.

On the other hand, in the case that the user performs an operation to complete display of images, the control section 27 detects the operation (step 9: Complete Display), and the process ends.

As described above, in the present embodiment, when the display control section 26 causes the display target image $Img_1$ to be displayed on the display screen, the bone number display setting section 22 receives selection regarding the display target bone numbers $BID_U$ to be displayed along with the display target image $Img_1$. The bone position specifying section 24 specifies the positions $CD_U$ of the bones, which are identified by the display target bone numbers $BID_U$, within the display target image $Img_1$, based on the bone information BI, in which the bone numbers $BID_U$ of vertebral bones and ribs and original bone position information $CO_n$ thereof within the three dimensional original image $Img_0$ are correlated, and the correspondence information $R_{0,1}$ that represents the correspondence of positions between the three dimensional original image $Img_0$ and the display target image $Img_1$. The display target bone numbers $BID_U$ are displayed along with the display target image $Img_1$ such that a user can visually recognize that the bones which are identified by the display target bone numbers $BID_U$ are displayed within the display target image $Img_1$ at the specified positions $CD_U$.

Accordingly, only bone numbers $BID_U$ which are desired by the user are displayed along with the display target image $Img_1$, from among the plurality of bone numbers corresponding to the bones within the display target image $Img_1$. Therefore, deterioration in visibility of the display target image $Img_1$ due to the bone numbers being overlapped thereon and displayed can be reduced, while maintaining the ease with which the positions of the bones identified by the selected bone numbers $BID_U$ are understood.

In addition, the user interface, an example of which was illustrated FIG. 4 as the bone number display setting screen, is employed to select the display target bone numbers $BID_U$. The user interface enables selection of display target bone numbers in groups of "vertebral bones" and "ribs", which include pluralities of bone numbers. Therefore, it is possible to select the bone numbers of all of the vertebral bones and all of the ribs as a bundle to be the display target bone numbers $BID_U$. Thereby, operations are simplified and operability is improved. Meanwhile, individual bone numbers are also enabled to be selected from the list box. Therefore, the display target bone numbers $BID_U$ can be finely set, according to the purposes of image diagnosis, user preference, and the like.

Further, the example of the user interface illustrated in FIG. 4 enables selection of "Display Representative Bone Number Only" as the display method DM. In the case that this option is selected, the representative bone number determining section 25 automatically determines representative bone numbers $BID_E$ which are effective for image diagnosis, from among the plurality of display target bone numbers $BID_U$, based on the predetermined rule that employs the type of the display target image $Img_1$, the type of the display target bone numbers $BID_U$, and the properties of the distribution of positions of bones which are identified by the display target bone numbers $BID_E$ within the display target image $Img_1$. The automatically determined representative bone numbers $BID_E$ are displayed along with the display target image $Img_1$. Therefore, only appropriate bone numbers $BID_E$ can be displayed, without the user having to consider the properties thereof. This contributes to an improvement in operability, while maintaining the visibility of the display target image $Img_1$.

Still further, the example of the user interface illustrated in FIG. 4 enables selection of "Display Near Target" as display position information DP. In the case that this option is selected, the display control section 26 automatically determines the display positions of the display target bone numbers $BID_U$ or the representative bone numbers $BID_E$ according to the type of the display target image $IMG_1$, and the type of the display target bone numbers $BID_U$ or the representative bone numbers $BID_E$. The display positions are determined such that the positions at which the bone numbers are displayed do not interfere with viewing of the display target image $Img_1$ during image diagnosis. Therefore, the visibility of the display target image $Img_1$ is improved further.

In the present embodiment, the control section 27 receives input of a switching operation for switching the display target image. The bone position specifying section 24 determines the positions $CD_U$ for each bone which is identified by the display target bone numbers $BID_U$, and the representative bone number determining section 25 determines the representative bone numbers $BID_E$ and the positions $CD_E$ of the bones identified thereby, for each image to be newly displayed. Therefore, the display control section 26 displays each new image such that the display target bone numbers $BID_U$ or the representative bone numbers $BID_E$ which are actually displayed are appropriately changed.

Modifications to the system structure, the processes, the module structure, and the user interface of the embodiment described above are included within the technical scope of the present invention, as long as such modifications do not stray from the spirit of the present invention. In addition, the embodiment described above is merely exemplary, and should not be utilized to interpret the technical scope of the present invention in a limiting manner.

For example, in the example of the bone number display setting screen illustrated in FIG. 4, the list box in the case that the display target bone numbers are set to "Individual Settings" may include only bone numbers $BID_n$ of bones which are detected within the three dimensional original image $Img_0$. Alternatively, only bone numbers $BID_n$ of bones which are present within a present display target image $Img_1$ from among bones detected within the three dimensional original image $Img_0$. In these cases, selection of the display target bone numbers $BID_U$ is not received at step 1 in the flow chart of FIG. 3. In the former case, selection of the display target bone numbers $BID_U$ may be received after obtaining the three dimensional original image $Img_0$ at step 3, and in the latter case, selection of the display target bone numbers $BID_U$ may be received after obtaining the display target image at step 4.

In addition, specification of the display target bone numbers $BID_U$ in the case that the option "Individual Settings" is selected may be performed without using the list box. Alternatively, a user may select display target bone numbers $BID_U$ by clicking on desired bones within a display target image $Img_1$ which is displayed on the display screen. In this case, the bone number display setting receiving section 22 may refer to the bone numbers $BID_n$ within the three dimensional original image $Img_0$ and the original bone position information $CO_n$ to specify the bone numbers of the bones included in the clicked positions, then designate these bone numbers as the display target bone numbers $BID_U$.

In the embodiment described above, the bone information BI is information which is attached to the three dimensional original image data $Img_0$. Alternatively, the bone information generating section 31 may generate a label image, in which a label value (bone number $BID_n$) is assigned to each bone within each bone region (original bone position information $CO_n$) within the three dimensional original image $Img_0$, based on the results of the image analyzing process. The label image is represented by three dimensional image data having the same coordinate system as the three dimensional original image data $Img_0$. In this case, the bone position specifying section 24 obtains an axial tomographic image from the label image having a slice number $m_0$, based on the slice number $m_0$ of a display target image $Img_1$, and extracts labeled regions having label values that correspond to display target bone numbers $BID_U$ from the axial tomographic image. The coordinate values of the labeled regions having the label values become the display bone position information $CD_U$.

In addition, the display target image obtaining section 23 is not limited to obtaining an axial tomographic image that constitutes the three dimensional original image data $Img_0$ as described in the above embodiment. Alternatively, the display target image obtaining section 23 may reconstruct a desired tomographic image into a coronal, a sagittal, or an oblique image, by administering MPR (Multi Planar Reconstruction) processes with respect to the three dimensional original image data $Img_0$. As further alternatives, an image obtained by administering a MIP/MinIP (Maximum Intensity Projection/Minimum Intensity Projection) process that extracts the maximum and minimum pixel values of search points along a plurality of sight lines that pass through the original image, an image that represents a desired curved surface within the original image generated by administering a CPR (Curved Planar Reconstruction) process on the original image, and a pseudo three dimensional image (hereinafter, referred to as "VR image") generated by administering a volume rendering process on the original image, may be obtained as the display target image $Img_1$. In these cases, it is necessary to correlate the positions of voxels in the three dimensional original image $Img_0$ that determine the pixel values of each pixel of the display target image $Img_1$, with each pixel of the display target image $Img_1$. Note that in the case that the display target image $Img_1$ is a VR image, the positions of the voxels that determine the pixel value of each pixel of the VR image cannot be strictly specified. However, voxels having the highest assignment values of opacity along sight lines within the three dimensional original image $Img_0$ that correspond to pixels of the VR image may be correlated to the pixels of the VR image.

The rules for determining the representative bone numbers $BID_E$ employed by the representative bone number determining section 25 are not limited to the rules described in the above embodiment. Examples of various other rules that may be employed are listed below.

Figure 7:
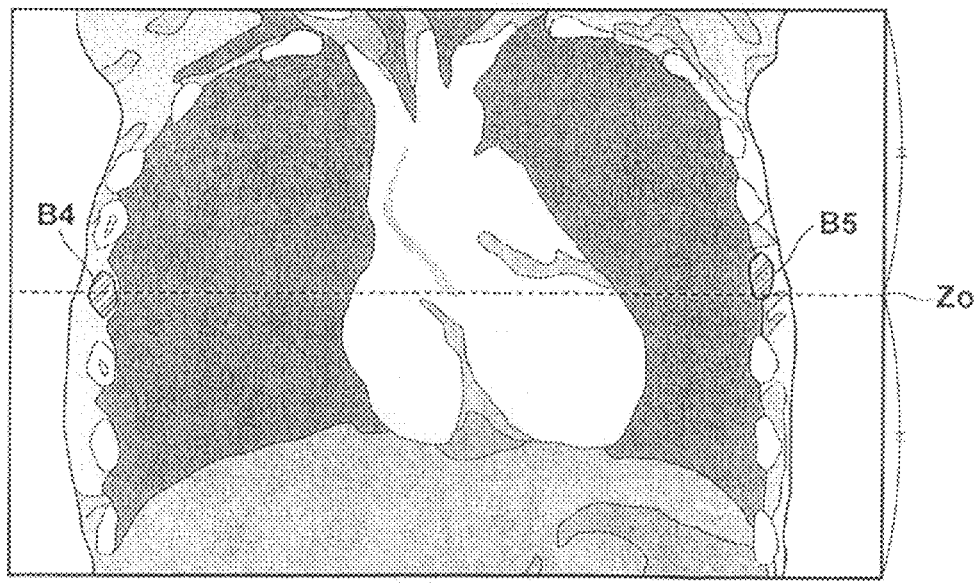
FIG. 7 is a diagram that schematically illustrates an example of a method for determining a representative bone number within a coronal tomographic image.

In the case that the display target image $Img_1$ is a coronal or a sagittal image, and the display target bone numbers $BID_U$ include the bone numbers for all ribs, the bone numbers for ribs B4 and B5 which are closest to a center point $Z_0$ in the vertical direction of the display target image $Img_1$ (the vertical direction of the subject) are designated as the representative bone numbers $BID_E$, as illustrated in FIG. 7.

In the case that the display target image $Img_1$ is a coronal or a sagittal image, and the display target bone numbers $BID_U$ include the bone numbers for all vertebral bones, the twelfth thoracic vertebra, the first lumbar vertebra, or both are designated as the representative bone numbers $BID_E$.

In the case that the display target image $Img_1$ is a coronal or a sagittal image, and the display target bone numbers $BID_U$ include the bone numbers for all vertebral bones, the vertebrae which are a predetermined distance from the upper edge or the lower edge of the image is designated as the representative bone number $BID_E$.

Figure 8:
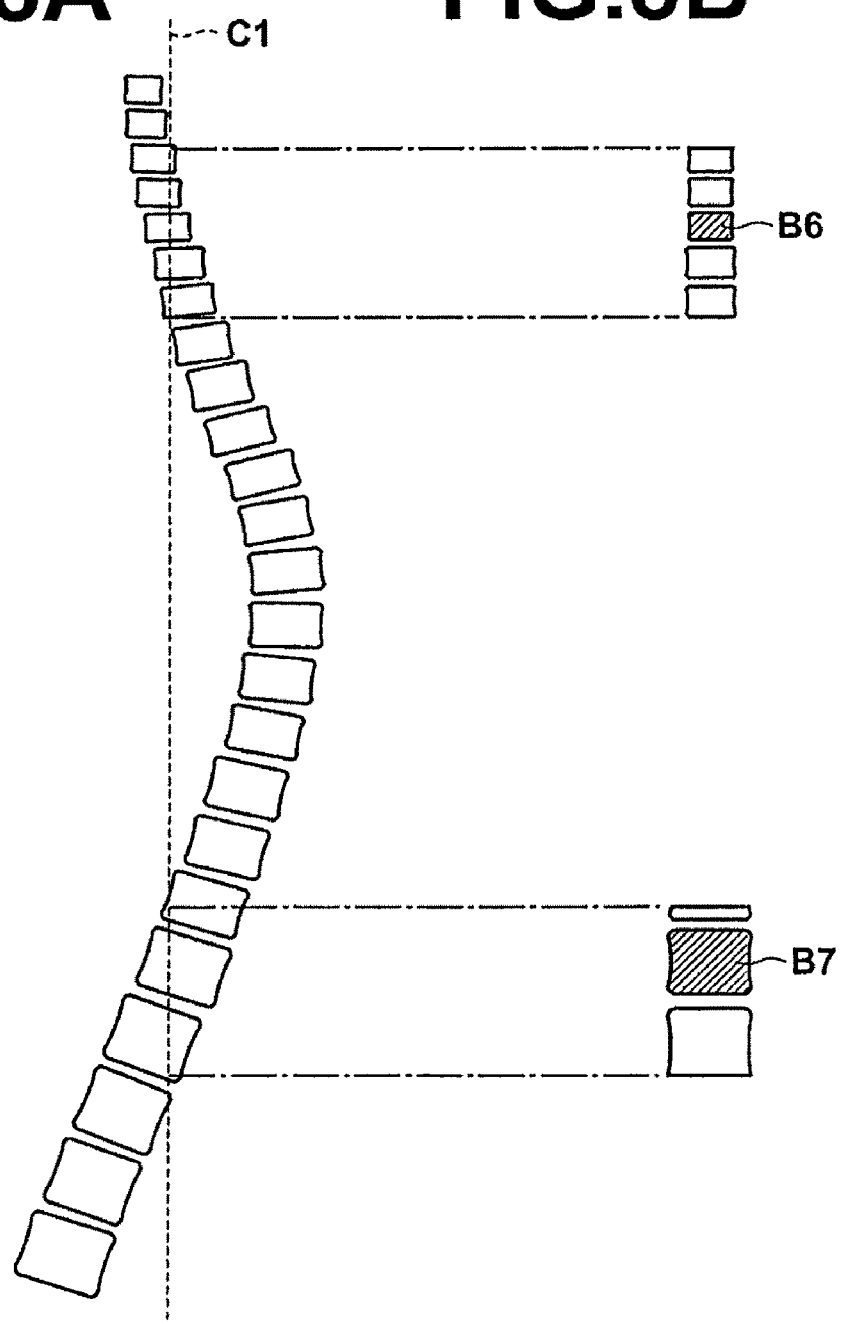
FIGS. 8A and 8B are diagrams that illustrate an example of a method for determining representative bone numbers for vertebral bones within a coronal tomographic image or a sagittal tomographic image.

In the case that the display target image $Img_1$ is a coronal or a sagittal image, the display target bone numbers $BID_U$ include the bone numbers for all vertebral bones, and the display target image $Img_1$ is a coronal tomographic image is that illustrated in FIG. 8B, in which the vertebral bones are not continuously displayed but only segments thereof are displayed due to the curvature of the spinal column as illustrated in the sagittal image of FIG. 8A, the bone numbers of the vertebral bones B6 and B7, which are positioned at the midpoints of each segment, are designated as the representative bone numbers $BID_E$.

The bone information generating section 31 may be provided in the image processing work station 2 or may be provided in the image server 3. Alternatively, the bone information generating section 31 may be provided in a different image processing server which is connected to the network 19. In addition, the bone information generating section 31 may not necessarily generate the bone information by administering the image analyzing process. Alternatively, bone information may be generated by tomographic images taken along three planes that perpendicularly intersect each other (an axial tomographic image, a coronal tomographic image, and a sagittal tomographic image) being displayed, and a user manually setting bone numbers while viewing the images.

In the embodiment described above, the names of the bones, such as the first thoracic vertebra and the first left rib, are used as the bone numbers. Alternatively, code values that correspond to the names of each bone may be correlated with the original bone position information or the display bone position information for each bone in information attached to the three dimensional original image data $Img_0$ or in a memory region. When the display control section 26 causes the bone numbers to be displayed on the display screen, the code values may be converted to the names of bones by using a conversion table or the like, then displayed.

<Supplemental Description>

Hereinafter, a description will be given of the image analyzing process for recognizing vertebral bone numbers and rib numbers administered by the bone information generating section 31. It is possible for the bone information generating section 31 to employ known processes, such as that disclosed by K. L. Weiss et al. (vertebral disk number recognizing process) and that disclosed in U.S. Patent Application Publication No. 20070110295 (rib number recognizing process). However, a description will be given of the processing method proposed by the present applicants in Japanese Patent Application No. 2008-092173.

Figure 9:
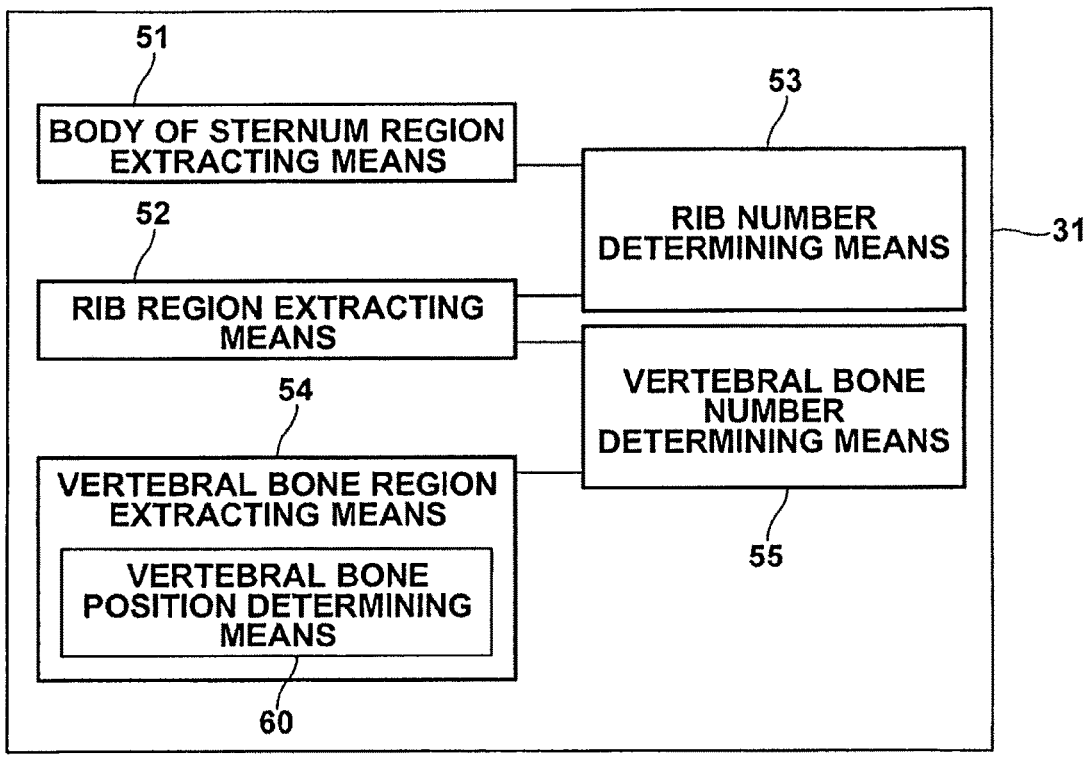
FIG. 9 is a block diagram that illustrates the construction of a bone information generating section that performs recognition of vertebral bone numbers and rib numbers.

FIG. 9 is a block diagram that illustrates the construction of the bone information generating section 31 that performs recognition of vertebral bone numbers and rib numbers. As illustrated in FIG. 9, the bone information generating section 31 is equipped with: a body of sternum region extracting means 51, a rib region extracting means 52, a rib number determining means 53, a vertebral bone region extracting means 54, and a vertebral bone number determining means 55. The body of sternum region extracting means 51 extracts a body of sternum region using the three dimensional original image $Img_0$ as input, and the rib region extracting means 52 extracts rib regions. The rib number determining means 53 determines the rib number of each extracted rib region, based on the position of the body of sternum and the position of each of the rib regions. The vertebral bone region extracting means 54 extracts vertebral bone regions, and the vertebral bone number determining means 55 determines the vertebra number of each of the vertebrae based on the rib number of each of the rib regions, the position of each of the rib regions, and the position of each of the vertebra regions.

The vertebral bone region extracting means 54 includes a vertebra position determining means 60 that determines the positions of the ends of vertebrae. The vertebral bone region extracting means 54 uses the information regarding the positions of the ends of a vertebra, and extracts a vertebral bone region which is segmented at the ends of the vertebra. The vertebral bone region represents each vertebrae, into which the vertebral column is separated.

Figure 10:
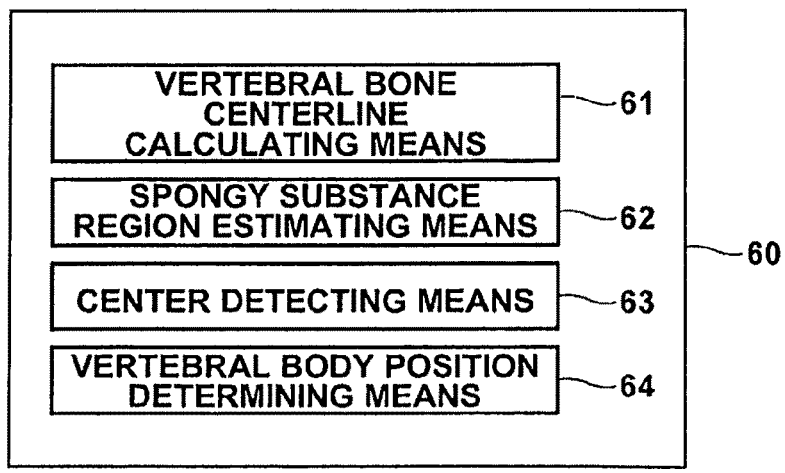
FIG. 10 is a schematic diagram that illustrates the configuration of a vertebra position determination means.

The vertebra position determining means 60 automatically calculates the positions of both ends of a vertebra in a tomographic image obtained, for example, by a CT apparatus. As illustrated in FIG. 10, the vertebra position determining means 60 includes a vertebral bone centerline calculating means 61, a spongy substance region estimating means 62, a center detecting means 63, and a vertebral body position determining means 64.

The vertebral bone centerline calculating means 61 obtains the centerline of vertebrae, based on a plurality of tomographic images that represent cross sectional planes of the vertebrae.

First, a spinal cord region is extracted from the three dimensional original image $Img_0$. As illustrated in FIG. 11, the spinal cord region exhibits a typical pattern in tomographic images. Therefore, it is possible to stably detect the spinal cord region from the tomographic images. Specifically, for example, a multiplicity of areas, each having a predetermined size, are set with respect to each pixel in each of the tomographic images. Then, a classifier generated by using a machine learning method is used to identify (judge or distinguish) whether each of the set areas is a spinal cord region, thereby detecting the spinal cord region.

Next, a spinal cord centerline is generated using the center points of a plurality of spinal cord regions that have been detected. A pixel which is present at the approximate center of a spinal cord region is set as the center point of the spinal cord region. It is not necessary for the center point to be located at the exact center of the spinal cord region. The center point may be a point which is substantially equidistant from the circumference (border) of the spinal cord region. Alternatively, the center point may be a point which is substantially equidistant from predetermined two ends of the spinal cord region. The center point may also be the center of gravity.

Further, a longitudinal cross sectional image (vertical cross sectional image) is generated by re-slicing the tomographic images along the spinal cord centerline in the direction of the body axis. As illustrated in FIG. 12, center point P5 of a spinal cord region obtained from each of the tomographic images is used as a base point, and the brightness value of each pixel on a straight line connecting point P3 and point P4, a straight line inclining counterclockwise from Y-axis by a degrees, is extracted. Then, the extracted brightness values of the pixels on the straight line connecting point P3 and point P4 in each of the tomographic images (the straight line corresponding to the direction of X-axis in the right half of FIG. 12) are piled (stacked) one on another in the order of slice numbers of the tomographic images (the order corresponding to the direction of Y-axis in the right half of the diagram illustrated in FIG. 12). Accordingly, longitudinal cross sectional image V is generated. Since a multiplicity of blood vessels or the like are present in the cardiac region (heart), a stable pattern is not obtained in the cardiac area. Therefore, the straight line connecting points P3 and P4 should be set in such a manner that the straight line passes the center point and the spinal area, but does not pass the cardiac area.

Further, the borders of vertebrae are detected in the longitudinal cross sectional image V In the longitudinal cross sectional image V, a spinal cord centerline L3 appears as a single curved line. Further, the spinal area including two trabecula lines, which have high CT values (pixel values), and a spongy substance region (a cancellous-bone area or a spongy-bone area) between the two trabecula lines appear on the left side of the spinal cord centerline L3. The spongy substance region has low CT values (pixel values). In the longitudinal cross sectional image V illustrated in FIG. 4, the pixels values are observed in the X-direction to obtain an edge that exhibits a large positive difference value on the ventral side of the spinal area. Further, an edge that exhibits a large negative difference value is obtained on the dorsal side of the spinal area. Further, linear transformation is performed on the spinal cord centerline L3 to fit the spinal cord centerline L3 to edge line L2 on the dorsal side of the spinal area, thereby obtaining edge curved line L5. Similarly, edge curved line L4 is obtained with respect to edge curved line L1 on the ventral side of the spinal area.

Figure 13:
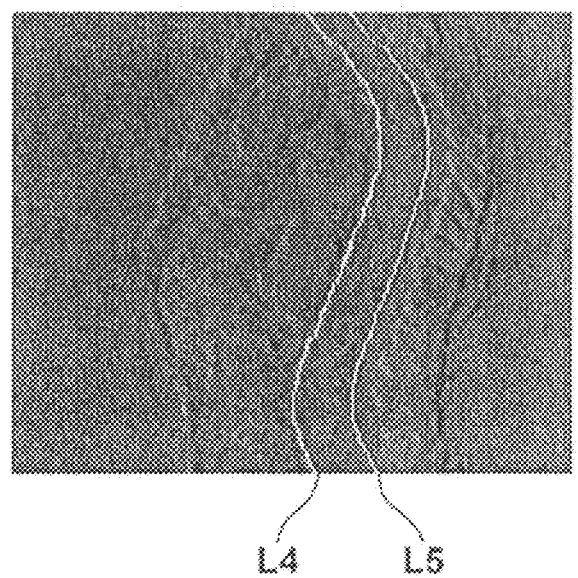
FIG. 13 is a diagram for explaining a method for calculating the left/right borders of vertebrae.

The obtained curved lines L4 and L5, as illustrated in FIG. 13, are the left/right borders of the vertebrae including the spinal area. Further, the centerline of the vertebrae and the width of the vertebra or vertebrae can be calculated based on the obtained curved lines L4 and L5, which are the left/right borders.

The spongy substance region estimating means 62 estimates a spongy substance region by using pixels in an area in the vicinity of the centerline of the vertebrae, which has been obtained by the vertebral bone centerline calculating means 61. Since lesions or abnormalities (deformations) of a vertebra or vertebrae may be present in the three dimensional original image $Img_0$ obtained by imaging, it is possible to more stably detect the spongy substance by using only the area in the vicinity of the centerline of the vertebrae instead of the entire area of the three dimensional original image $Img_0$. If the spongy substance region, which can be relatively stably detected based on the image pattern thereof, is extracted first and the intervertebral regions are obtained based on the detected spongy substance region, it is possible to accurately obtain the intervertebral regions.

Figure 14:
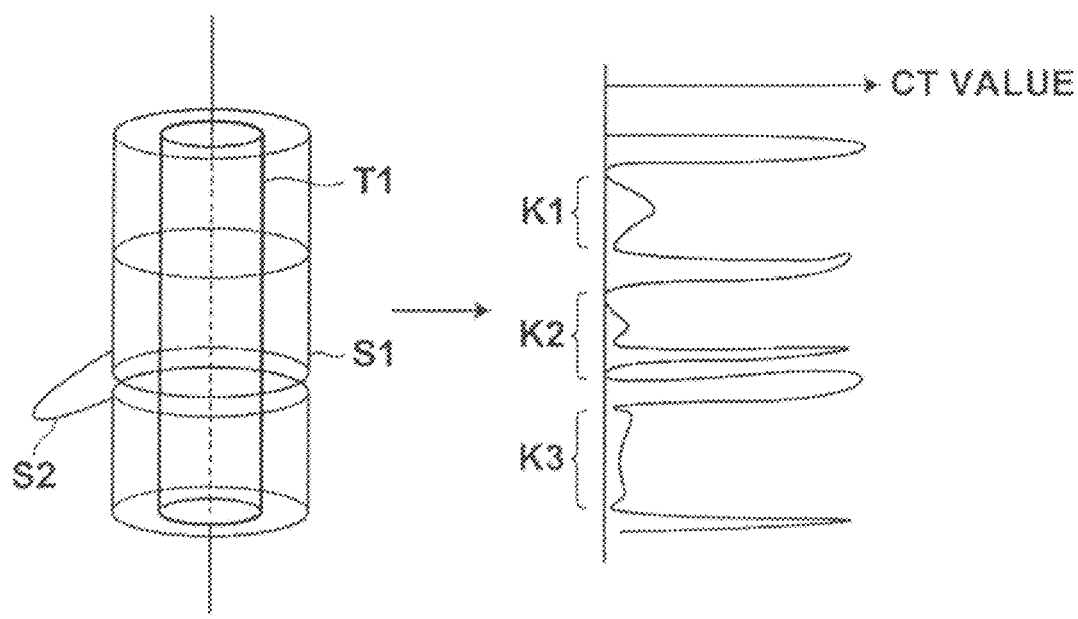
FIG. 14 is a diagram for explaining a method for determining the positions of vertebrae.

FIG. 14 is a conceptual diagram illustrating vertebrae, vertebral bodies and the like. The cylinder (Tube) S1 illustrated in FIG. 14 represents a vertebral body or vertebral bodies. The surface of the cylinder S1 corresponds to the lateral cortex region of the vertebral body, and the top plate and the bottom plate of the cylinder S1 correspond to the up/down endplates of the vertebral body, respectively. Projection S2 represents a bone proliferation (growth) region. Tube portion T1 represents a region in the vicinity of the center of the spinal cord. When CT values (pixel values) of the tube portion T1 are added in the transverse direction (horizontal direction), a graph as illustrated on the right side of FIG. 6 is obtained. In some cases, an intervertebral region is lost and not present in tomographic images by a so-called virtual volume effect. However, as illustrated in the graph of FIG. 14, low CT value (pixel value) areas (for example K1, K2 and K3) that correspond to the spongy substance regions appear in tomographic images. However, in the graph, a trough at an intervertebral region may not be clearly distinguished because of the bone proliferation region of projection S2. Therefore, when the spongy substance region is damaged (crushed) as in a three-dimensional image representing the human body of a patient suffering from a serious compression fracture, and there is a possibility that the CT values (pixel values) in the spongy substance region become high, the addition value of the CT values (pixel values) is not used for judgment. Instead, the edge in the direction of the body axis is detected. If the edge in the direction of the body axis is detected, the spongy substance region can be detected even if the compression fracture is present in the image.

The center detecting means 63 detects the three dimensional center of the spongy substance region estimated by the spongy substance region estimating means 62 in each of the vertebral bodies. The three-dimensional center of the spongy substance region can be obtained by performing machine learning in advance. In the machine learning, the feature value of each pixel of a plurality of sample images including spongy substance regions is learned. A classifier obtained by machine learning is used, and a score indicating the degree of inclusion of a spongy substance region in the region in the vicinity of the centerline of the vertebrae is calculated based on the feature values of pixels in the vicinity of the centerline of the vertebrae. Further, the three dimensional center of the spongy substance region is detected based on the score.

The vertebral body position determining means 64 calculates the positions of both ends of each of the vertebral bodies in the body axis direction, based on the three-dimensional center of the spongy substance region in each of the vertebral bodies that has been detected by the center detecting means 63. The vertebral body position determining means 64 determines the position of each of the vertebral bodies based on the calculated positions of both ends of each of the vertebral bodies. For example, a middle point of the three-dimensional centers of the spongy substance regions in two vertebral bodies that are adjacent to each other is determined as an intervertebral region of the two vertebral bodies. Alternatively, the position of the cortex of the vertebral body may be detected by detecting the maximum of the sum of CT values (pixel values) between the three-dimensional centers of the spongy substance regions in two vertebral bodies that are adjacent to each other (or the intensity of the edge). Further, the ends of the vertebral bodies may be determined based on the detected positions of the cortexes of the vertebral bodies.

The rib region extracting means 52 separates rib regions, each including a rib, from each other to extract the rib regions from the three dimensional original image $Img_0$ that represents a human body.

For example, the rib regions may be extracted by using the method disclosed in U.S. Patent Application Publication No. 20060062425 (hereinafter, referred to as "Reference Document 1"). Reference Document 1 discloses a technique based on high speed tracing for extracting a rib region from a three dimensional image. This technique may be used to extract ribs, and to obtain rib regions, each representing a single rib.

Figure 15:
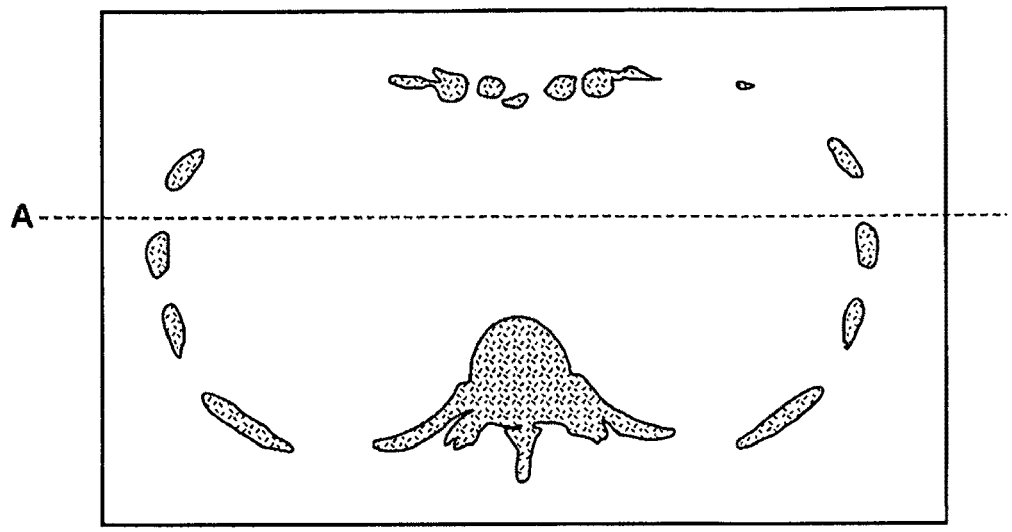
FIG. 15 is a diagram that illustrates an example of a tomographic image of a region including a vertebra and ribs.

Alternatively, the rib regions may be detected by using a density histogram of bone areas. FIG. 15 is a tomographic image of a vertebra and rib portions. First the centerline of the vertebra and the width (transverse width) of the vertebra are obtained. For this purpose, in the bone area illustrated in FIG. 15, an area which is lower than centerline A in the transverse direction of the body surface of a subject is projected onto the vertical axis, and the density histogram is generated (the centerline A is a line in the transverse direction of the body of the subject, which is perpendicular to the anterior/posterior direction of the body, at an anterior/posterior-direction center of a cross section perpendicular to the direction of the body axis of the subject connecting the head and the feet of the subject).

Figure 16:
FIG. 16 is a diagram that illustrates density histogram of bone regions.

FIG. 16 illustrates a density histogram of bone areas that has been generated as described above. In the histogram illustrated in FIG. 16, a high peak is present at the middle of the histogram, and small peaks (low peaks) are present at the left side and the right side of the histogram. It is recognized that the rib portion in the tomographic image illustrated in FIG. 15 forms the small peaks in FIG. 16, and that the vertebra in the tomographic image illustrated in FIG. 15 forms the highest peak in FIG. 16, because the largest bone area is present in the vertebra. Therefore, the highest peak at the middle of the histogram is extracted from the histogram illustrated in FIG. 16. Further, an area corresponding to the highest peak is detected as a vertebral bone region.

Figure 17:
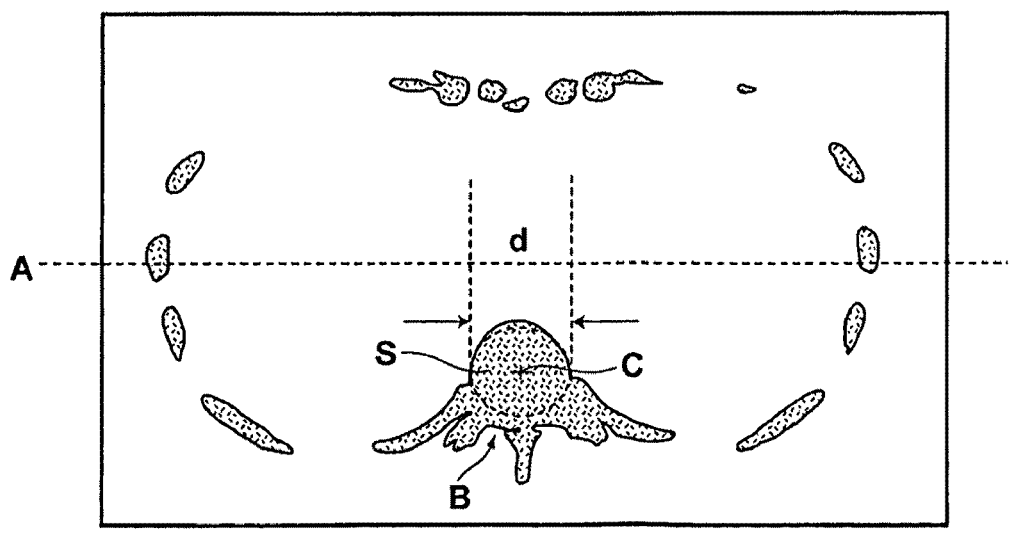
FIG. 17 is a diagram that shows the center and the width of a vertebra.

Then, as illustrated in FIG. 17, a circle S is fitted into an upper portion (anterior portion) of detected vertebral bone region B to obtain a center C of the vertebra and a width d of the vertebra. Further, the vertebral bone region, left/right rib regions and a sternum area are recognized by using the center C of the vertebra and the width d of the vertebra.

Figure 18:
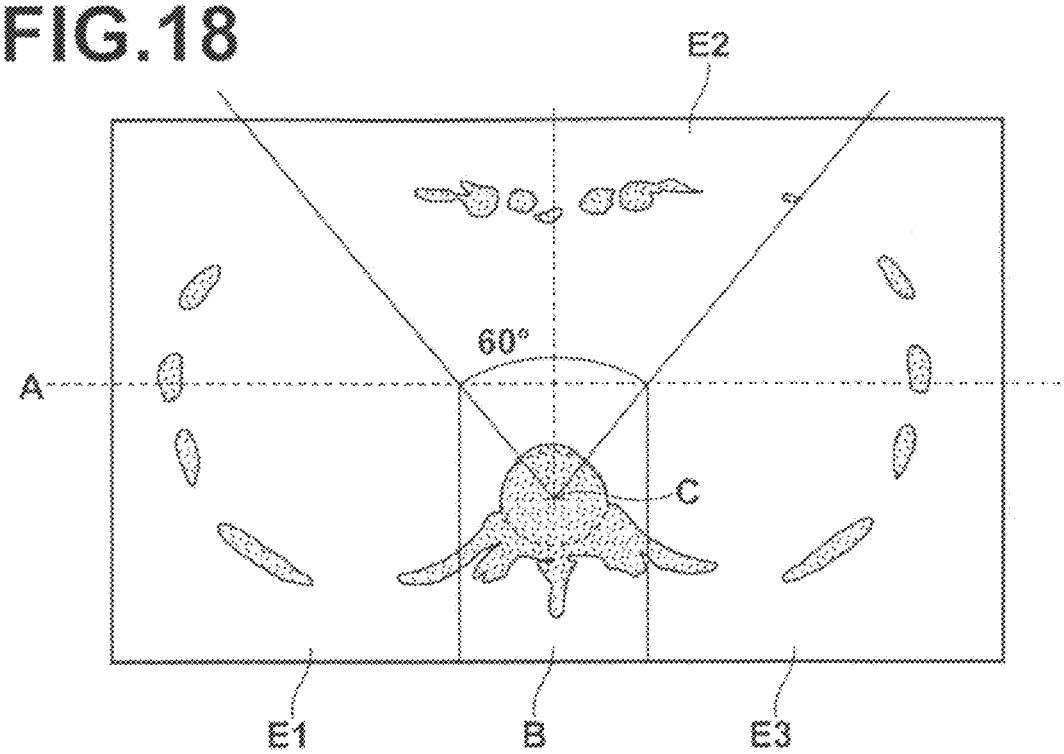
FIG. 18 is a diagram in which a tomographic image is divided into a vertebra area, a right rib area, a sternum area, and a left rib area.

As illustrated in FIG. 18, two half lines (rays), each forming an angle of 60 degrees with respect to the center C of the vertebra, which has been obtained as described above, are drawn on the upper side of the center C of the vertebra. Further, two straight lines that are orthogonal to the centerline A in the transverse direction of the body surface of the subject are drawn in such a manner that the center C of the vertebra is positioned at the center of the two straight lines. The distance between the two straight lines is the width of the vertebral bone region. The width of the vertebral bone region is set in such a manner that the width is 1.5 times longer than the aforementioned width d of the vertebra. As described above, the two half lines and the two straight lines that are orthogonal to the centerline A in the transverse direction of the body surface of the subject are drawn. Further, the bone area in a tomographic image illustrated in FIG. 18 is divided into four areas. The divided four areas are determined as vertebral bone region B, right rib region E1, sternum area E2, and left rib region E3.

As described above, bones are recognized as unit parts, such as the vertebra, the right rib, the sternum, and the left rib. Each part is recognized in all of the tomographic images of the three dimensional original image $Img_0$. Further, the areas of ribs detected from each of the tomographic images are piled on each other in the order of the slice numbers of the images, and the area formed by the piling is extracted as a rib region.

Figure 19:
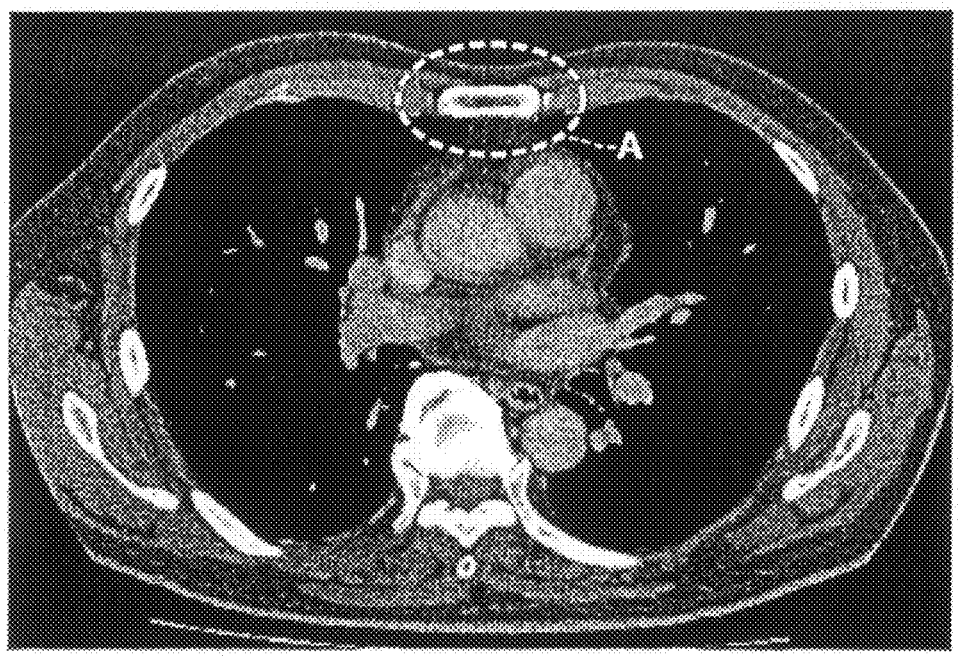
FIG. 19 is a diagram that illustrates an example of a tomographic image of a body of sternum.

The body of sternum region extracting means 51 extracts the body of sternum region from the three dimensional original image $Img_0$. In tomographic images, the body of sternum appears as a rectangular area that has substantially the same thickness therethrough, as illustrated in FIG. 19. Further, the body of sternum includes a lumen (spongy substance) (please refer to portion A in FIG. 19). Therefore, the body of sternum can be detected by pattern recognition. In a tomographic image (cross-section) of the chest, the body of sternum appears at a position closer to the anterior side of the human body, which is opposite to the position of the vertebra. Therefore, a rectangular area is detected from an area close to the anterior surface of the human body (or an area in the vicinity of the anterior surface of the human body) in each tomographic image. Further, the rectangular area detected in each of the tomographic images is piled (stacked) one on another in the order of the slice numbers of the tomographic images, and an area formed by piling the rectangular areas is extracted as a body of sternum region.

Figure 20:
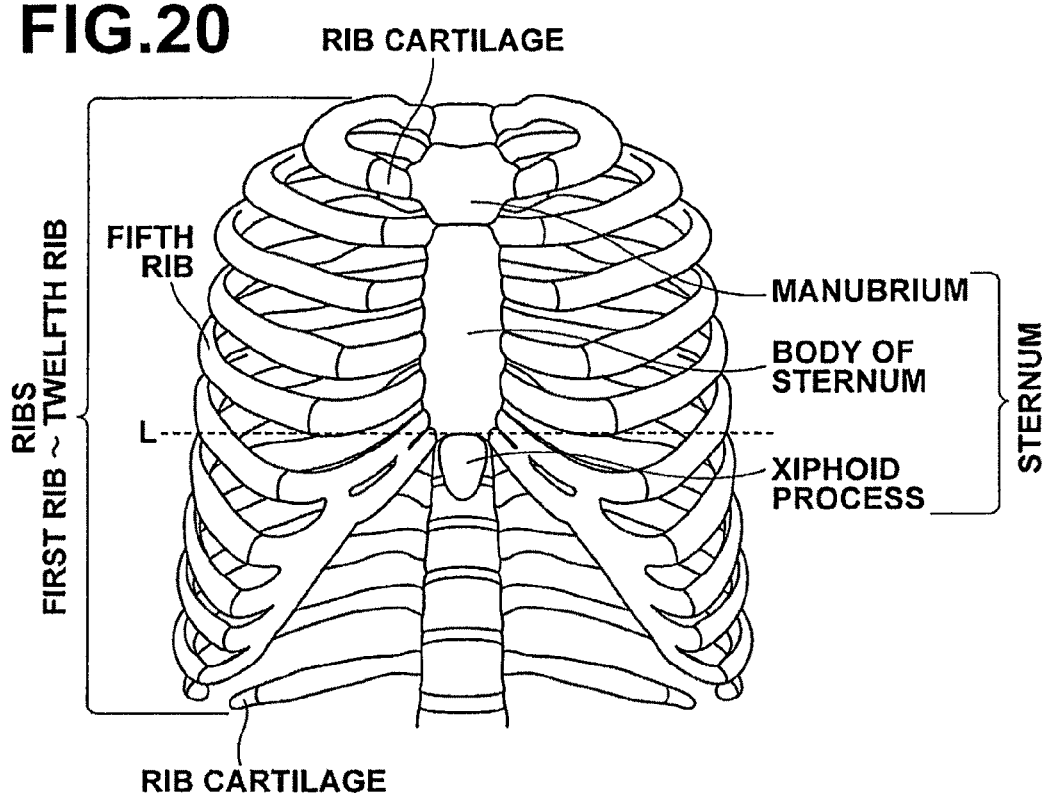
FIG. 20 is a diagram for explaining connections between the body of sternum and ribs.

The rib number determining means 53 determines the rib number based on the manner in which the rib region and the body of sternum region are connected to each other. As illustrated in FIG. 20, anatomically, second ribs through ten ribs are connected to the body of sternum. Further, substantially the entire area of each of first ribs through fifth ribs is positioned above lower border L of the body of sternum. Therefore, it is possible to identify, as the fifth rib, the rib of a rib region, the substantially entire area of which is located at a higher position than the lower border L of the body of sternum, and that is located at the lowest position among all of the rib regions that are connected to the body of sternum (the rib number is five or fifth). Further, the rib number of each of the other rib regions is determined based on the fifth rib region in the order of arrangement of the rib regions.

The vertebral bone number determining means 55 determines the vertebra number of each of the vertebral bone regions based on the rib numbers of the rib regions and the manner in which the rib regions and the vertebral bone regions are connected to each other.

Figure 21:
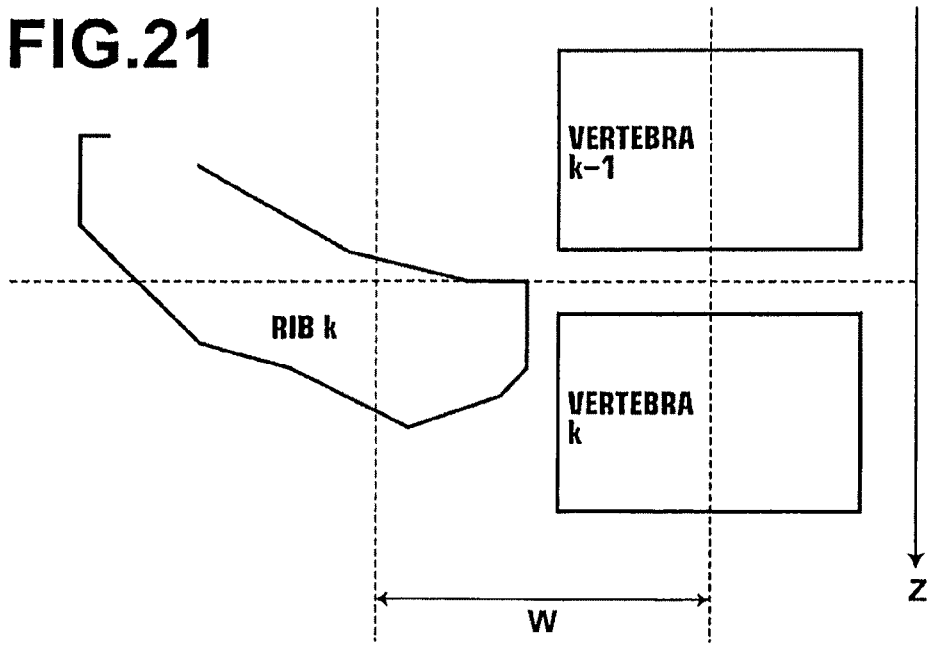
FIG. 21 is a diagram for explaining a connection between a vertebra and a rib.

One method for obtaining information regarding which vertebral bone region a rib region is connected to is illustrated in FIG. 21. In FIG. 21, first, a certain width W is determined with respect to the centerline of the vertebral bone region, in other words, a certain distance W is set from the centerline of the vertebral bone region (for example, the width of the vertebra may be used as the width W). A portion of a rib region of rib number k, the portion being present within a range determined by the distance W from the centerline, is projected onto Z-axis in the diagram illustrated in FIG. 21 to obtain a range in which the rib region appears in the direction of the Z-axis. Similarly, the vertebral bone regions are projected onto the Z-axis in the diagram illustrated in FIG. 21 to obtain a range in which each of the vertebral bone regions appears in the Z-axis. Further, one of the vertebral bone regions that has a largest overlapping area with the rib region having the rib number k is judged as a vertebra connected to the rib having the rib number k. Further, the vertebra number of the vertebral bone region is determined as k.

Figure 22:
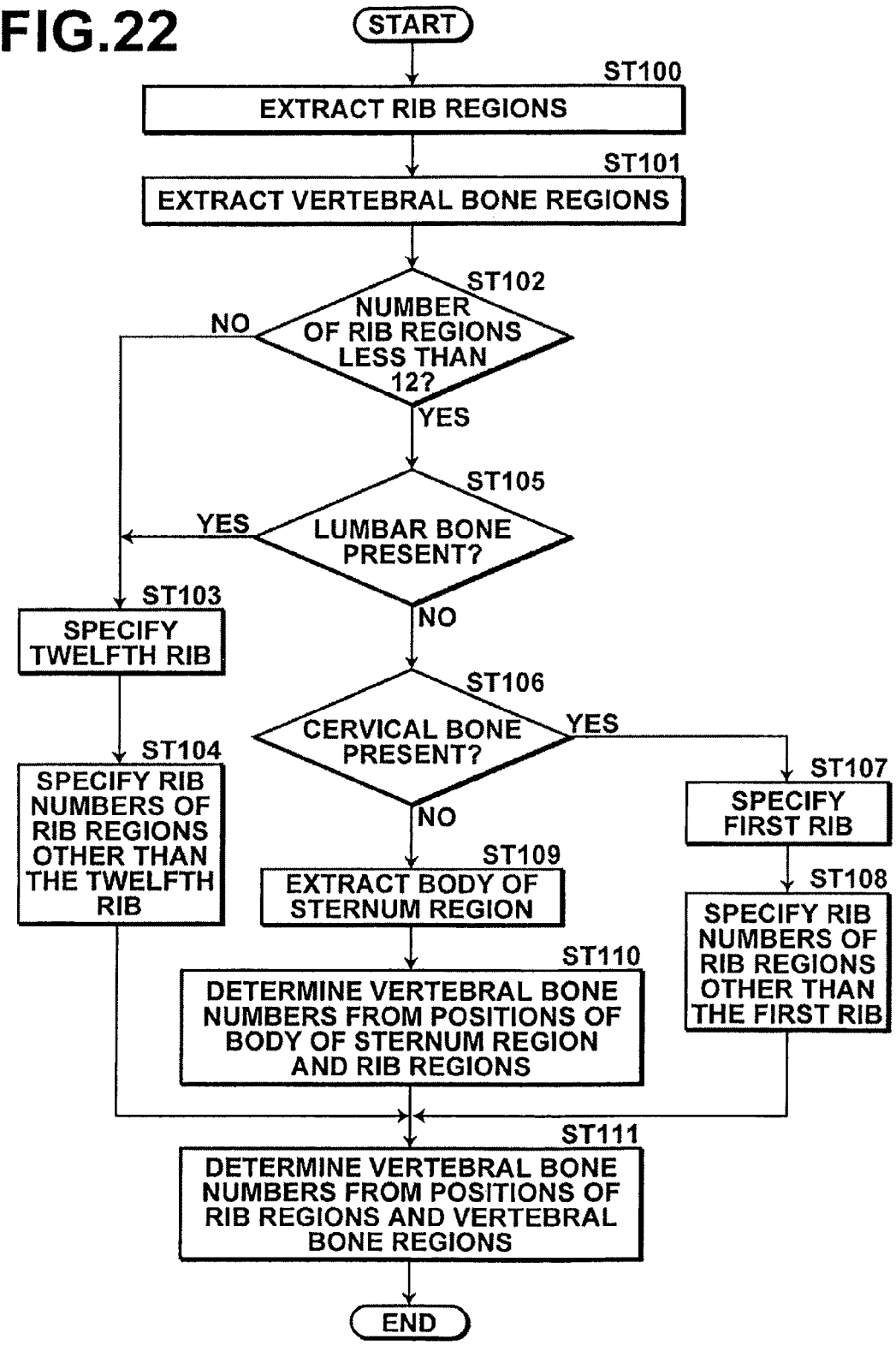
FIG. 22 is a flowchart that illustrates the steps of a process for recognizing rib numbers and vertebra numbers.

Next, the steps of the process performed by the bone information generating section will be described, with reference to the flowchart of FIG. 22.

First, the rib region extracting means 52 extracts all of rib regions imaged within a three dimensional original image $Img_O$ (step ST100). Next, the vertebral bone region extracting means 54 extracts a spinal cord region from the three dimensional original image $Img_O$. Further, the vertebral bone region extracting means 54 automatically calculates the positions of both ends of each of vertebrae, and separates the vertebrae into each of vertebral bone regions (step ST101).

Then, the number of the extracted rib regions is counted (step ST102). When the number of the rib regions is 12, the twelfth rib region is identified (step ST103), and the twelfth rib region is used as a base region. Further, rib numbers are sequentially assigned to other rib regions, based on the twelfth rib region, in descending order (11, 10, . . . 1) toward the upper side (step ST104).

When the number of the rib regions is less than 12, judgment is made as to whether a lumbar vertebra (or a hip bone) is imaged in the three dimensional original image $Img_O$. If the lumbar vertebra (or a hip bone) is imaged in the three dimensional original image $Img_O$ (step ST105), the lowest rib of the ribs is imaged. Therefore, the rib number of the lowest rib region is identified as 12, in other words, the lowest rib region is identified as the twelfth rib region (step ST103), and the twelfth rib region is used as a base region. Further, rib numbers are sequentially assigned to other rib regions, based on the twelfth rib region, in descending order (11, 10, . . . ) toward the upper side (step ST104). When the number of the rib regions is less than 12, and the lumbar vertebra (or a hip bone) is not imaged in the three-dimensional image, judgment is made as to whether a cervical vertebra (or a neck bone) is imaged. If the cervical vertebra (or a neck bone) is imaged, the highest rib of the ribs is imaged (step ST106). Therefore, the rib number of the highest rib is identified as 1, in other words, the highest rib is identified as the first rib (step ST107), and the first rib region is used as a base region. Further, rib numbers are sequentially assigned to other rib regions, based on the first rib region, in ascending order (2, 3, . . . ) toward the lower side (step ST108).

Further, the vertebral bone number determining means 55 determines the vertebra number of each of the vertebral bone regions based on the rib numbers of the rib regions and the manner in which the rib regions and the vertebral bone regions are connected to each other (step ST111).

When the number of the rib regions is less than 12, and neither the lumbar vertebra (or a hip bone) nor the cervical vertebra (or a neck bone) is imaged, the body of sternum region extracting means 51 extracts a body of sternum region from the three-dimensional image (step ST109). Further, the rib number determining means 53 determines the rib number based on the manner in which the rib region is connected to the body of sternum region (step ST110).

Next, the vertebral bone number determining means 55 determines the vertebra number of each of the vertebrae based on the rib numbers of the rib regions and the manner in which the rib regions and the vertebral bone regions are connected to each other (step ST111).

In the aforementioned case, when all of 12 rib regions are recognized, or when the first rib or the twelfth rib is recognized, the rib numbers are identified without recognizing the body of sternum. Alternatively, the body of sternum may always be recognized to identify the position of the body of sternum and the position of the fifth rib, and the rib numbers of other ribs may be identified.

What is claimed is:

1. An image display apparatus, comprising:
   image display means for displaying a two dimensional display target image, which represents a cross-sectional surface of a three dimensional image, in which the positions of each pixel are enabled to correspond to positions within an original image that represents a subject in the three dimensional image, based on the original image;
   structure information obtaining means for obtaining structure information, in which structure identifying information that identifies each of a plurality of predetermined anatomical structures within the subject and structure position information that represents the positions of the anatomical structures within the original image are correlated;
   structure identifying information specifying means for receiving specification regarding which of the structure identifying information, each corresponding to an anatomical structure, is specified as display target structure identifying information to be displayed along with the display target image; and
   structure position specifying means for specifying the position of the anatomical structure, which is identified by the structure identifying information, within the display target image, based on the structure information and the correspondence of positions between the original image and the display target image;
   wherein the structure identifying information specifying means receives specification of a group constituted by a plurality of anatomical structures, to enable specification of structure identifying information that identifies the anatomical structures included in the group as the display target structure identifying information; and
   the image display means displaying the display target structure identifying information along with the display target image in response to receiving the specification of the display target structure identifying information, and the display target structure identifying information is displayed within the display target image at a display position determined corresponding to the position specified by the structure position specifying means, according to a preset rule.

2. The image display apparatus as defined in claim 1, further comprising:
   representative structure determining means for determining representative structure identifying information to be displayed along with the display target image from among the plurality of pieces of structure identifying information, each of which identifies an anatomical structure included in a group, based on a predetermined rule, in the case that a structure group identifying information is specified; and wherein:
   the image display means displays only the determined representative structure identifying information from among the structure identifying information of the plurality of anatomical structures that belong to the group along with the display target image; and
   the predetermined rule is defined by at least one of: the distribution of positions, which have been specified by the structure position specifying means, of the plurality of anatomical structures included in the group which is identified by the specified structure group identifying information within the target display image; the structure identifying information of the plurality of anatomical structures; and the type of the display target image.

3. The image display apparatus as defined in claim 2, wherein:
the structure identifying information specifying means is further capable of receiving specification regarding whether the image display means is to display only the representative structure identifying information along with the display target image, or the image display means is to display the structure identifying information for all of the anatomical structures that belong to the group which is identified by the structure group identifying information.

4. The image display apparatus as defined in claim 1, wherein:
the structure identifying information specifying means is further capable of receiving specification regarding the display position of the display target structure identifying information.

5. The image display apparatus as defined in claim 4, wherein:
the structure identifying information specifying means is capable of receiving specification regarding the display position such that the display target structure identifying information is displayed in the vicinity of the anatomic structure which is identified by the display target structure identifying information.

6. The image display apparatus as defined in claim 1, wherein:
the structure identifying information specifying means is equipped with a user interface for receiving specifications by selection from among a plurality of selectable options.

7. The image display apparatus as defined in claim 1, wherein:
the anatomical structures are the bones of the subject,
the structure identifying information are bone numbers,
the structure position information are the positions of the bones,
the structure information are bones information, and
the display target structure identifying information are display target bone numbers.

8. An image display control method for displaying a two dimensional display target image, which represents a cross-sectional surface of a three dimensional image, in which the positions of each pixel are enabled to correspond to positions within an original image that represents a subject in the three dimensional image, based on the original image, comprising the steps of:
obtaining structure information from an image database, in which structure identifying information that identifies each of a plurality of predetermined anatomical structures within the subject and structure position information that represents the positions of the anatomical structures within the original image are correlated;
receiving specification regarding which of the structure identifying information, each corresponding to an anatomical structure, is specified as display target structure identifying information to be displayed along with the display target image; and
specifying the position of the anatomical structure, which is identified by the structure identifying information, within the display target image, based on the structure information and the correspondence of positions between the original image and the display target image;
wherein the structure identifying information specifying step the specification of a group constituted by a plurality of anatomical structures is received, to enable specification of structure identifying information that identifies the anatomical structures included in the group as the display target structure identifying information; and
displaying the display target structure identifying information along with the display target image, on a display, in response to receiving the specification of the display target structure identifying information, and the display target structure identifying information is displayed within the display target image at a display position determined corresponding to the position specified by the structure position specifying step, according to a preset rule.

9. A non-transitory computer readable medium having recorded therein a program that causes a computer to execute an image display control method for displaying a two dimensional display target image, which represents a cross-sectional surface of a three dimensional image, in which the positions of each pixel are enabled to correspond to positions within an original image that represents a subject in the three dimensional image, based on the original image, comprising the procedures of:
obtaining structure information, in which structure identifying information that identifies each of a plurality of predetermined anatomical structures within the subject and structure position information that represents the positions of the anatomical structures within the original image are correlated;
receiving specification regarding which of the structure identifying information, each corresponding to an anatomical structure, is specified as display target structure identifying information to be displayed along with the display target image; and
specifying the position of the anatomical structure, which is identified by the structure identifying information, within the display target image, based on the structure information and the correspondence of positions between the original image and the display target image;
wherein the structure identifying information specifying step the specification of a group constituted by a plurality of anatomical structures is received, to enable specification of structure identifying information that identifies the anatomical structures included in the group as the display target structure identifying information; and
displaying the display target structure identifying information along with the display target image in response to receiving the specification of the display target structure identifying information, and the display target structure identifying information is displayed within the display target image at a display position determined corresponding to the position specified by the structure position specifying procedure, according to a preset rule.

10. The image display apparatus as defined in claim 7, wherein the bones are vertebral bones or ribs.

* * * * *